United States Patent [19]

Greenquist et al.

[11] 4,447,529

[45] May 8, 1984

[54] PREPARING HOMOGENEOUS SPECIFIC BINDING ASSAY ELEMENT TO AVOID PREMATURE REACTION

[75] Inventors: Alfred C. Greenquist; Patricia A. Rupchock; Richard J. Tyhach, all of Elkhart; Bert Walter, South Bend, all of Ind.

[73] Assignee: Miles Laboratories, Inc., Elkhart, Ind.

[21] Appl. No.: 280,260

[22] Filed: Jul. 6, 1981

[51] Int. Cl.$^3$ .................. G01N 33/54; G01N 33/52
[52] U.S. Cl. ........................ 435/7; 422/56; 435/805; 436/530; 436/810; 436/815
[58] Field of Search .............. 435/4, 7, 177, 188, 435/805, 810; 23/230 B; 422/55, 56, 57, 58; 424/8, 12; 252/408; 436/530, 810, 815

[56] References Cited

U.S. PATENT DOCUMENTS

| | | | |
|---|---|---|---|
| 3,905,767 | 9/1975 | Morris et al. | 422/58 |
| 4,042,329 | 8/1977 | Hochstrasser | 422/58 |
| 4,168,146 | 9/1979 | Grubb et al. | 435/7 |
| 4,226,978 | 10/1980 | Boguslasler et al. | 435/7 |
| 4,235,601 | 11/1980 | Deutsch et al. | 23/230 B |
| 4,238,565 | 12/1980 | Hornby et al. | 435/188 |
| 4,258,001 | 3/1981 | Pierce et al. | 422/56 |
| 4,299,916 | 11/1981 | Litman et al. | 435/7 |
| 4,340,564 | 7/1982 | Harte et al. | 422/56 |
| 4,362,697 | 12/1982 | Tabb | 422/57 X |
| 4,363,874 | 12/1982 | Greenquist | 422/57 X |

*Primary Examiner*—Sidney Marantz
*Attorney, Agent, or Firm*—Edward H. Gorman, Jr.

[57] ABSTRACT

A homogeneous specific binding assay element, a method for its preparation, and a method for its use in determining a ligand in or the ligand binding capacity of a liquid sample. The test element comprises a solid carrier incorporated with reagents for a homogeneous specific binding assay system which produces a detectable response, usually an electromagnetic radiation signal, that is a function of the presence or amount of the ligand in or the ligand binding capacity of the sample. Also a method for preparing a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent reactive with the label conjugate, which method comprises (a) incorporating the carrier with the reagent reactive with the label conjugate in a first liquid and drying the carrier; and then (b) incorporating the carrier of (a) with the label conjugate in a liquid effective to prevent reaction with the reagent reactive with the label conjugate prior to contact of the element with the sample and drying the carrier.

18 Claims, 16 Drawing Figures

PROSTHETIC GROUP LABEL IMMUNOASSAY (a) RECONSTITUTION REACTION

LABELED DRUG + APOENZYME ⟶ ACTIVE ENZYME
(INACTIVE)

(b) ANTIBODY BINDING REACTION (c) COMPETITIVE BINDING REACTION

SUBSTRATE-LABELED IMMUNOFLUORESCENT ASSAY (a) ENZYMATIC REACTION (b) ANTIBODY BINDING REACTION (c) COMPETITIVE BINDING REACTION

QUENCHING IMMUNOFLUORESCENT ASSAY (a) ANTIBODY BINDING REACTION (b) COMPETITIVE BINDING REACTION

PREPARING HOMOGENEOUS SPECIFIC BINDING ASSAY ELEMENT TO AVOID PREMATURE REACTION

BACKGROUND OF THE INVENTION

1. Field of the Invention

This invention relates to test devices or elements, their preparation and their use in determining a ligand in or the ligand binding capacity of a liquid sample based on a specific binding assay, e.g., immunoassay, principle. In particular, this invention relates to solid state carrier elements incorporated with homogeneous specific binding assay reagents.

2. Brief Description of the Prior Art

Test devices in the form of test strips and similar solid state analytical elements have become commonplace in the analysis of various types of samples, particularly biological fluids. Test strips designed for detecting clinically significant substances in biological fluids, such as serum and urine, have been advantageous in the diagnosis of disease.

Test strips of various types have been known and used for many years in a wide variety of fields, from the most familiar pH test paper devices to in vitro diagnostic devices for the detection of various urine and blood components such as glucose, protein, occult blood and so forth (e.g., as described in U.S. Pat. Nos. 3,164,534; 3,485,587; and 3,012,976). Reagent compositions found in such conventional test strips interact with the constituent or constituents to be determined by direct chemical reaction and, for this and other reasons, have limited sensitivity, being applied to the detection of substances that are present in liquid samples at concentrations in the millimolar range or above.

On the other hand, the development of specific binding assay techniques has provided useful analytical methods for determining various organic substances of diagnostic, medical, environmental and industrial importance which appear in liquid mediums at very low concentrations. Specific binding assays are based on the specific interaction between the ligand, i.e., the bindable analyte under determination, and a binding partner therefor. Where one of the ligand and its binding partner is an antibody and the other is a corresponding hapten or antigen, the assay is known as an immunoassay.

In conventional specific binding assay techniques, a sample of the liquid medium to be assayed is combined with various reagent compositions. Such compositions include a label conjugate comprising a binding component incorporated with a label. The binding component in the label conjugate participates with other constituents, if any, of the reagent composition and with the ligand in the medium under assay. This forms a binding reaction system in which two species, a bound-species and a free-species, of the label conjugate are formed. In the bound-species, the binding component of the label conjugate is bound by a corresponding binding partner e.g., an antibody, whereas in the free-species, the binding component is not so bound. The relative amount or proportion of the label conjugate that results in the bound-species compared to the free-species is a function of the presence (or amount) of the ligand to be detected in the test sample.

Where the label conjugate in the bound-species is essentially indistinguishable in the presence of the label conjugate in the free-species by the means used to monitor the label, the bound-species and the free-species must be physically separated in order to complete the assay. This type of assay is referred to in the art as "heterogeneous". Where the bound-species and free-species forms of the label conjugate can be distinguished in the presence of each other, the separation step can be avoided, and the assay is said to be "homogeneous".

The first discovered type of highly sensitive specific binding assay was the radioimmunoassay which employs a radioactive isotope as the label. Such an assay necessarily must follow the heterogeneous format since the monitorable character of the label is qualitatively unchanged in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules. Such homogeneous specific binding assay systems provide a detectable response, e.g, an electromagnetic radiation signal, such as chemiluminescence, fluorescence emission, or color change, realted to the present of amount of the ligand under assay in the liquid sample.

Commercially available test means for performing specific binding assays are usually in the form of test kits comprising a packaged combination of containers holding solutions or rehydratable compositions of the reagents necessary for carrying out the assay. To perform the actual assay method, aliquots of such solutions must be manually or instrumentally dispensed into a reaction vessel with the sample. If manually dispensed, the assay consequently requires the time and skill of a technician, and if instrumentally dispensed, the assay consequently requires the expense and maintenance of dispensing apparatus.

Solid phase test devices have been applied to heterogeneous specific binding assays in attempts to overcome the inconveniences and disadvantages of the requisite separation step. A commonly used solid phase device of this type comprises a nonporous surface, such as the interior surface of a test tube or other vessel, to which antibody is affixed or coated by adsorption or covalent coupling. U.S. Pat. Nos. 3,826,619; 4,001,583; 4,017,597; and 4,105,410 relate to the use of antibody coated test tubes in radioimmunoassays. Solid phase test devices have also been used in heterogeneous enzyme immunoassays (U.S. Pat. Nos. 4,016,043 and 4,147,752) and in heterogeneous fluorescent immunoassays (U.S. Pat. Nos. 4,025,310 and 4,056,724; and British Patent Spec. No. 1,552,374).

The use of such heterogeneous specific binding assay test devices is exemplified by the method of U.S. Pat. No. 4,135,884 relating to a so-called "gamma stick". The test device is incorporated with the antibody reagent and is brought into contact with the liquid sample and with the remaining reagents of the reaction system, principally the label conjugate. After an incubation period, the solid phase device is physically removed from the reaction solution and the label measured either in the solution or on the test device.

Similar devices where the antibody reagent is entrapped in a matrix such as a gel or paper web are described in U.S. Pat. Nos. 3,925,017; 3,970,429; 4,138,474;

3,966,897; 3,981,981 and 3,888,629 and in German OLS No. 2,241,646. Likewise, devices for use in heterogeneous specific binding assays wherein the antibody reagent is fixed to a matrix held in a flowthrough column are know (U.S. Pat. Nos. 4,036,947; 4,039,652; 4,059,684; 4,153,675; and 4,166,102). The test device is usually incorporated with less than all of the necessary reagents for carrying out the assay and is merely a means for rendering more convenient the necessary separation step.

Finally, heterogeneous specific binding assay test devices have been described wherein most or all of the necessary reagents are incorporated with the same carrier element, and wherein reagent/sample contacts and separation of the free- and bound-phases are accomplished by capillary migrations along the carrier element (U.S. Pat. Nos. 3,641,235; 4,094,647 and 4,168,146). The devices described in such patents are generally considered difficult to manufacture and susceptible to irreproducibility due to the complex nature of the many chemical and physical interactions that take place along the carrier element during performance of an assay.

The application of homogeneous specific binding assay reagent systems to solid state test devices would provide great advantages to the routine user of such assay systems. The determination of ligands appearing in very low concentrations in liquid samples would be simplified to the steps of contacting the device with the sample and measuring, either by visual observation or by instrumental means, the resulting signal. Reagents would be provided in a solid form, with no need to store, dispense or mix liquid reagents as required when using the prior art test kits. Solid state devices would also be much more adaptable to automation than the prior art liquid systems.

The prior art lacks a detailed teaching of how to apply homogeneous specific binding assay reagent systems to solid state test devices. British Patent Spec. No. 1,552,607, commonly assigned herewith, describes homogeneous specific binding assay systems employing various novel labels, including chemiluminescent labels, enzyme substrate labels and coenzyme labels. At page 23, lines 12 et seq of this patent there is the suggestion of incorporating the assay reagents with various carriers including liquid-holding vessels or insoluble, porous, and preferably absorbent, matrices, fleeces, or blocks; gels; and the like.

German OLS No. 2,537,275 describes a homogeneous specific binding assay reagent system and poses the possibility of using slides or strips incorporated with antibody in performing the assay. In this suggestion, the label conjugate would be first mixed with the sample and thereafter the antibody incorporated test device contacted with the reaction mixture. After a suitable incubation time, it is proposed that the test device would be rinsed with buffer, dried, and then the signal (fluorescence) measured. Thus, this German OLS poses a test device and assay method much like those already known for heterogeneous specific binding assay techniques wherein the test device is immersed in the liquid reaction mixture, incubated, thereafter removed, washed, and finally read. Additionally, the proposed test device does not incorporate all of the binding assay reagents with the carrier element. Specifically, only the antibody is proposed to be incorporated with the carrier element with the label conjugate being separately added to the sample under assay prior to contact with the proposed test device.

Copending U.S. Ser. No. 255,521 filed on Apr. 20, 1981 and commonly assigned herewith discloses a method for determining the presence of a ligand in, or the ligand binding capacity of, a liquid test sample. The method comprises the steps of adding to said liquid sample a label conjugate comprising said ligand, or a binding analogue thereof, chemically bound to a label, contacting said sample with a test device comprising a carrier matrix incorporated with reagents which, when combined with said label conjugate, produce a homogeneous specific binding assay system which produces a detectable response which is a function of the presence of said ligand or said ligand binding capacity, thereby producing said response, and measuring said response.

Copending U.S. Ser. No. 202,378, filed on Oct. 30, 1980 and commonly assigned herewith, discloses a homogeneous specific binding assay device, a method for its preparation, and a method for its use in determining a ligand in, or the ligand binding capacity of, a liquid sample. This includes, for example, a test device for determining a ligand in or the ligand binding capacity of a liquid sample, comprising (a) reagents for a homogeneous specific binding assay system which produces a detectable response that is a function of the presence of the ligand in or the ligand binding capacity of the sample, and (b) a solid carrier member incorporated with said reagents.

Copending U.S. Ser. No. 253,147, filed on Apr. 10, 1981 and commonly assigned herewith discloses a homogeneous specific binding assay device for use in determining a ligand in a liquid sample, comprising (a) a reagent composition including a complex of (i) a label conjugate comprising a label component coupled to said ligand or a specific binding analog thereof, and (ii) a specific binding partner for said ligand, said label providing a detectable response, or interacting with a detectant system to provide a detectable response, which is different when the label conjugate is bound by said binding partner compared to when it is not so bound and (b) a carrier incorporated with said complex.

SUMMARY OF THE INVENTION

The present invention provides a homogeneous specific binding assay test element, a method for its preparation, and a method for its use in determining a ligand in or the ligand binding capacity of a liquid sample. The test element comprises (a) reagents for a homogeneous specific binding assay system which produces a detectable response that is a function of the presence, in a qualitative or quantitative sense, of the ligand in or the ligand binding capacity of the liquid sample under assay, and (b) a solid carrier incorporated with the reagents. Particularly, the invention provides a method for preparing a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent reactive with the label conjugate, which method comprises (a) incorporating the carrier with the reagent reactive with the label conjugate in a first liquid and drying the carrier; and then (b) incorporating the carrier of (a) with the label conjugate in a liquid effective to prevent its reaction with the reagent reactive with the label component prior to contact of the element with the sample and drying the carrier.

By precisely following the steps of the above defined method it is possible to incorporate all the reagents necessary for a specific binding assay into an integral single layer element.

DESCRIPTION OF THE PREFERRED EMBODIMENTS

Figure 1A:
FIGS. 1-14 are graphical representations of procedures used in and data obtained from the experiments described in the examples.
Figure 1A:
Figure 1A:
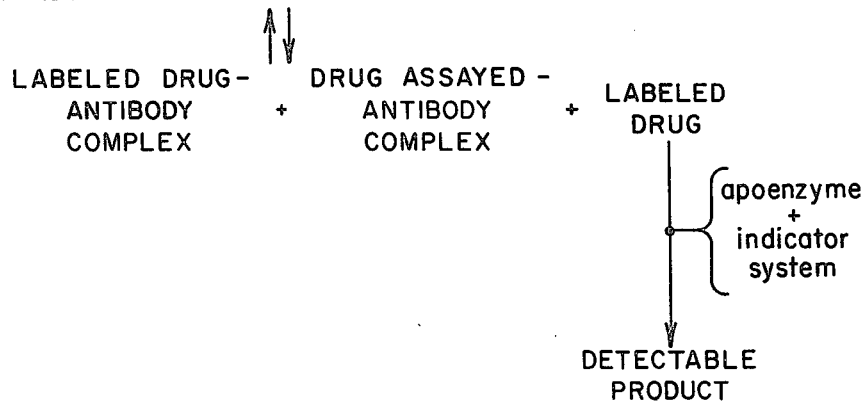

The present invention provides a test device for use in carrying out homogeneous specific binding assays, e.g., immunoassays, having all of the convenience features of conventional analytical test strips and other test elements of similar design. As in the case of such conventional devices, the present invention provides a solid carrier, usually a matrix of one sort or another, incorporated with all of the reagents necessary to perform a given assay whereby the user has only the task of bringing the test device into contact with the sample to be tested and measuring the resulting response. Where the entire process is automated, an instrument for performing the same manipulations can have a much simpler design than one having to deal with conventional liquid chemistry systems now used for performing homogeneous specific binding assays.

1. HOMOGENEOUS SPECIFIC BINDING ASSAYS

Reagents for any homogeneous specific binding assay system may be incorporated in the present test device. In general, homogeneous specific binding assay techniques are based on the special interaction between (1) a conjugate of a binding component and a label and (2) a binding partner to the binding component in the conjugate, whereby a characteristic of the label is different when the label conjugate is bound by the binding partner compared to when such conjugate is not so bound. The affected characteristic of the label may be of any measurable nature, for instance, a chemical or physical quality of the label. In some cases, the affected characteristic is a chemical reactivity in a predetermined reaction which involves the formation or breaking of chemical bonds, covalent or noncovalent. In other cases, the affected characteristics is a physical characteristic of the label which can be measured without chemical reaction.

In the majority of cases, the present test device will incorporate homogeneous specific binding assay reagents which respond to the ligand or its binding capacity in the sample in an immunochemical manner. That is, there will be an antigen-antibody or hapten-antibody relationship between reagents and/or the ligand or its binding capacity in the sample. Such assays therefore are termed immunoassays and the special interaction between the label conjugate and its binding partner is an immunochemical binding. Thus, in such instances, the binding component of the label conjugate is an antigen, hapten or antibody (or a fragment thereof) and the binding partner is its corresponding immunochemical binding partner. However, it is well understood in the art that other binding interactions between the label conjugate and the binding partner serve as the basis of homogeneous specific binding assays, including the binding interactions between hormones, vitamins, metabolites, and pharmacological agents, and their respective receptors and binding substances.

Where the sample is being assayed to determine the presence or amount of a particular ligand therein, the reagents for the homogeneous specific binding assay technique comprise, in the usual case, (1) a label conjugate composed of the ligand, or a binding analog thereof, chemically coupled to the label, (2) a binding partner for the ligand, e.g., an antibody or fragment thereof, a natural receptor protein, and the like, and (3) any ancillary reagents necessary for measuring the labeling substance in the label conjugate. A limiting amount of the binding substance is introduced so that any ligand in the sample will complete with the label conjugate for binding to the binding partner. The distribution of the label between the bound-species and the free-species will therefore determine the magnitude of the detectable response from the label, which in turn will be a function of the presence of the ligand. Another scheme for determining a ligand is presented where the label conjugate is composed of a labeled binding partner of the ligand and, upon binding to the ligand, the label is affected in terms of its detectable response. Where ligand binding capacity of the sample is under assay, the label conjugate will be composed of the ligand, or a binding analog thereof, chemically coupled to the label whereby the capacity of the sample to bind the label conjugate, such as due to the presence of a binding partner of the ligand in the sample, determines the effect made on the detectable signal from the label.

Several different homogeneous specific binding assay systems are known in the art, and the following are examples, without limiting the scope of the present invention, of some such systems contemplated for use in the present test device. The following systems are listed according to the nature of the label used.

(a) Enzyme Prosthetic Group Labels

In this system, where the label is a prosthetic group of an enzyme, the ability of a catalytically inactive apoenzyme to combine with the prosthetic group label to form an active enzyme (holoenzyme) is affected by binding of the label conjugate with its binding partner. Resulting holoenzyme activity is measurable by conventional detectant systems to yield an ultimately detectable signal. Assay systems of this type are described in commonly assigned, copending application Ser. No. 45,423, filed June 4, 1979 (corresponding to published British Patent Spec. No. 2,023,607). A particularly preferred prosthetic group-label assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide.

In such preferred assay scheme, the FAD-labeled conjugate is preferably of the formula:

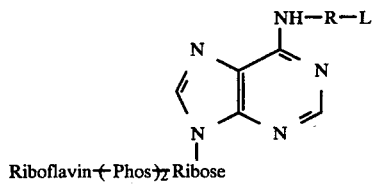

wherein Riboflavin-(-Phos)₂Ribose represents the riboflavin-pyrophosphate-ribose residue in FAD, R is a linking group, and L is the binding component, e.g., the ligand or analog thereof. A schematic representation of this type of assay is shown in FIG. 1a of the drawings.

(b) Enzyme Substrate Labels

In this system, the label is selected so that the label conjugate is a substrate for an enzyme and the ability of the enzyme to act on the substrate-label conjugate is affected, either in a positive or negative sense, by binding of the label conjugate with its binding partner. Action of the enzyme on the substrate-label conjugate produces a product that is distinguishable in some feature, usually a chemical or physical feature such as chemical reactivity in an indicator reaction or such as a photometric character, e.g., fluorescence or light absorption (color). Assay systems of this type are described in commonly assigned, copending applications Ser. Nos. 894,836, filed Apr. 10, 1978 (corresponding to published German OLS No. 2,618,511) and 87,819, filed Oct. 23, 1979; and in *Anal. Chem.* 48:1933 (1976), *Anal. Biochem.* 77:55 (1977) and *Clin. Chem.* 23:1402 (1977). A particularly preferred substrate-label assay scheme employs a label conjugate of the structure

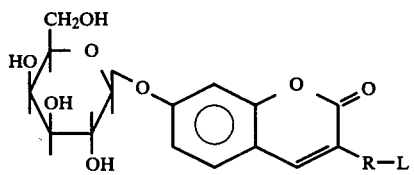

wherein R is a linking group and L is the binding component, e.g., the ligand or analog thereof, whereby the ability of the enzyme β-galactosidase to cleave the conjugate yielding a product distinguishable by its fluorescence is inhibited by binding of the conjugate with its binding partner.

Figure 1B:
Figure 1B:
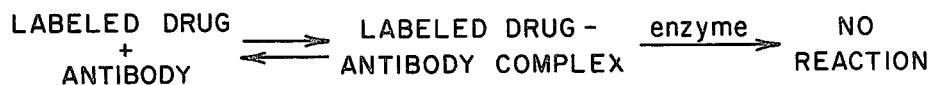
Figure 1B:
Figure 1B:
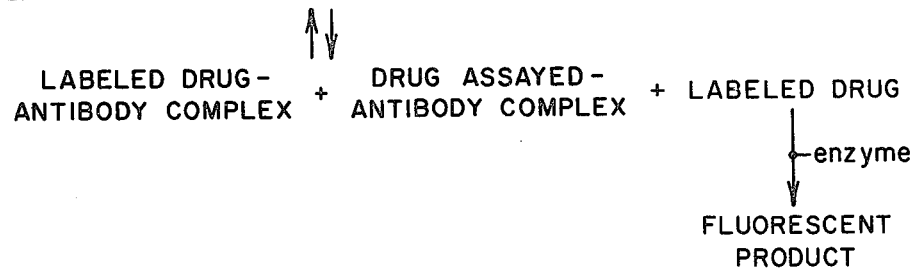

An important application of this technique is in aminoglycoside antibiotic assays wherein the binding component is the antibiotic under assay or a binding analog thereof. A schematic representation of the principles of this type of homogeneous immunoassay for a drug is shown in FIG. 1b of the drawings. In assays where antibody is used as the binding partner it has been found that other aminoglycoside antibiotics can cross-react with the antibody for the antibiotic under assay. Thus, such other antibiotics qualify as binding analogs and may be used to form the label conjugate. Further, the antibody qualifies as a reagent for use in assays for the cross-reacting antibiotic. For example, in an assay for gentamicin it has been found that, with an appropriate antiserum, the binding component in the label conjugate can be gentamicin itself or sisomicin which cross-reacts. Thus, gentamicin antiserum and a labeled sisomicin conjugate could be used in an assay for gentamicin. Specificity problems are not encountered in clinical situations because it would be known what antibiotic was administered and only one aminoglycoside antibiotic is administered at a time.

The β-galactosyl-umbelliferone-label conjugates formed are of the formula:

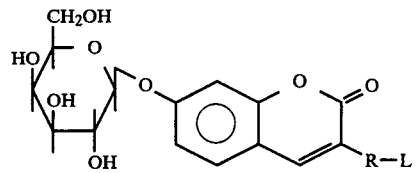

wherein R is a linking group terminating in an amino-linking group, preferably carbonyl; L is an aminoglycoside antibiotic coupled by a covalent bond to the linking group R through a primary amino group therein; and n is an integer from 1 to the total number of primary amino groups in the selected antibiotic.

(c) Coenzyme Labels

The label conjugate in this system is composed in its label portion, by a coenzyme-active functionality. The ability of the coenzyme label to participate in an enzymatic reaction is affected by binding of the label conjugate with its binding partner. The rate of the resulting enzymatic reaction is measurable by conventional detectant systems to yield an ultimately detectable signal. Assay systems of this type are described in commonly assigned, copending application Ser. No. 894,836, filed Apr. 10, 1978 (corresponding to published German OLS No. 2,618,511); and in *Anal. Biochem.* 72:271 (1976), *Anal. Biochem.* 72:283 (1976) and *Anal. Biochem.* 76:95 (1976).

(d) Enzyme Modulator Labels

The label conjugate in this system is composed, in its label portion, of an enzyme modulating functionality such as an enzyme inhibitor or stimulator. The ability of the modulator label to modulate the activity of an enzyme is affected by binding of the label conjugate with its binding partner. The rate of the resulting enzymatic reaction is measurable by conventional detectant systems to yield an ultimately detectable signal. Assay systems of this type are described in commonly owned U.S. Pat. No. 4,134,792.

(e) Enzyme Labels

In this system, the label is an enzyme and the activity of the enzyme label is affected by binding of the label conjugate with its binding partner. Resulting enzyme activity is measurable by conventional detectant systems to yield an ultimately detectable signal. Assay systems of this type are described in U.S. Pat. Nos. 3,817,837 and 4,043,872.

(f) Quenchable Fluorescent Labels

Figure 1C:
Figure 1C:
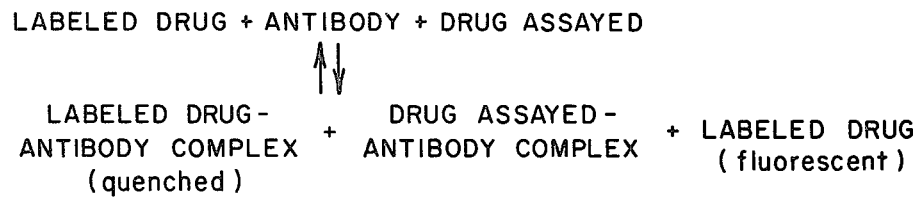

The label conjugate in this sytem is composed in its label portion, of a fluor the fluorescence of which is quenched in some measurable degree when the label conjugate is bound by its binding partner, usually a protein such as an antibody. The fluorescent label is measured directly, with its fluorescence being the detectable signal. Assay systems of this type are described in U.S. Pat. Nos. 4,160,016 and in *J. Clin. Path.* 30:526 (1977). A schematic representation of the principles of this type of assay is shown in FIG. 1c of the drawings.

(g) Chemically-Excited Fluorescent Labels

In this system, the label is again a fluor, however, the ability of the fluor label to be chemically excited to an energy state at which it fluoresces is affected by binding of the label conjugate with its binding partner. Chemical excitation of the label is usually accomplished by exposure of the fluor label to a high energy compound formed in situ. Assay systems of this type are described in commonly-owned, copending application Ser. No. 4,580, filed Jan. 18, 1979.

(h) Double Antibody Steric Hindrance Labels

Another assay system is the double antibody immunoassay system described in U.S. Pat. Nos. 3,935,074 and 3,998,943. The label conjugate comprises two epitopes, one of which participates in the immunological reaction with the ligand and anti-ligand antibody and the other of which is bindable by a second antibody, with the restriction that the two antibodies are hindered from binding to the label conjugate simultaneously. The second epitope can be a fluorescent substance the fluorescence of which is quenched by the second antibody binding, or may participate in an ancillary competitive binding reaction with a labeled form of the second epitope for binding to the second antibody. Various detectant systems are possible in such a system as described in the aforementioned patents. Related assay systems are described in U.S. Pat. Nos. 4,130,462 and 4,161,515 and in British Patent Spec. No. 1,560,852.

(i) Energy Transfer Labels

In this system, the label is one member of an energy transfer donor-acceptor pair and the binding partner is conjugated with the other of such pair. Thus, when the label conjugate is bound by its binding partner, the energy expression of the donor component of the pair is altered by transferance to the acceptor component. Usually, the donor is a fluor and the acceptor is a quencher therefor, which quencher may or may not be a fluor as well. In such embodiment, the detectable signal is fluorescence, but other detectant systems are possible also. Such assay systems are described in U.S. Pat. Nos. 3,996,345; 4,174,384; and 4,199,559 and in British Patent Spec. No. 2,018,424.

(j) Other Labels

Other homogeneous specific binding assay systems described in the art which can be used in the present invention include the use of labels such as:
(i) nonenzymic catalysts, such as electron transfer agents (see U.S. Pat. No. 4,160,645);
(ii) nonenzymic chemiluminescers (see commonly owned, copending application Ser. No. 894,836 referred to above);
(iii) "channeling" labels (see British Pat. Spec. No. 2,018,986);
(iv) "particle" labels (see British Pat. Spec. No. 2,019,562); and
(v) labeled liposome particles (see U.S. Pat. No. 4,193,983).

2. LIGAND

The present assay may be applied to the detection of any ligand for which there is a specific binding partner and, conversely, to the detection of the capacity of a liquid medium to bind a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-liproprotein, erythropoietin, transferrin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as heptatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilimicin, penicillin, tetracycline, terramycin, chloromycetin, and actinomycetin; nucleosides and nucleotides such as adenosine diphosphate (ADP), adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepine, doxorubicin, nortryptiline, methotrexate, imipramine, lidocaine, procainamide, N-acetyl-procainamide, the amphetamines, the catecholamines, and the antihistamines. the catecholamines, and the antihistamines.

The liquid medium to be assayed can be a naturally occurring or artifically formed liquid suspected to contain the ligand, and usually is a biological fluid or a dilution thereof. Biological fluids that can be assayed include serum, plasma, urine, saliva, and amniotic and cerebrospinal fluids.

3. CARRIER MEMBER

The carrier member of the present invention can take on a multitude of forms, and is therefore intended as being broad in context. It can be mono- or multi-phasic, comprising one or more appropriate materials or mediums of similar or different absorptive or other physical characteristics. It can be hydrophobic or hydrophilic, bibulous or nonporous. In its most efficient embodiment the carrier member can be carefully tailored to suit the characteristics of the particular homogeneous specific binding assay system to be employed.

Thus, as used herein, the term "carrier member" can comprise any substance, matrix, or surface capable of being incorporated with specific binding assay reagents. It can take on many known forms such as those utilized for chemical and enzymatic reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of papers is suggested in British Pat. No. 1,369,139. Another British Pat. No. 1,349,623, suggests the use of a light-permeable meshwork of thin filaments as a cover for an underlying paper carrier element. This reference also suggests impregnating the paper with part of a reagent system and impregnating the meshwork with other potentially incompatible chemical or enzymatic reagents. French Pat. No. 2,170,397 teaches the use of carrier members having greater than 50% polyamide fibers therein. U.S. Pat. No. 4,046,514 discloses the interweaving or knitting of filaments bearing reagents in a reactant system. All such carrier member concepts can be employed in the present invention, as can others. Preferably the carrier member comprises a bibulous material, such as filter paper, whereby a solution or suspension of the reagents of the specific binding assay system is used to impregnate the carrier member. It can comprise a system wherein the ingredients are homogeneously combined with the carrier member in a fluid or semi-fluid state, which later hardens or sets, thereby entrapping the ingredients.

Whichever material is chosen for the carrier member, whether it be porous to permit incorporation of ingredients such as through saturation with a solution containing them, whether it be nonporous such as to support or create a continuous coating, whether it be woven or knitted, whatever its composition or configuration, its selection will in any event be dictated by anticipated use and by the reagent system.

4. PREPARATION OF THE TEST DEVICE

A method of preparing the test device is provided by the present invention. This is a method for preparing a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent reactive with the label conjugate, which method comprises (a) incorporating a carrier with the reagent reactive with the label conjugate in a first liquid and drying said carrier; and (b) incorporating the carrier of (a) with the label conjugate in a liquid effective to prevent its reaction with the reagent reactive with the label conjugate and drying the carrier. The reactive reagent can comprise, for example, a specific binding partner for the ligand or a specific binding partner for the ligand and a component which is reactive with the label conjugate to cleave the label component from the ligand moiety or specific binding analog thereof.

In a preferred embodiment, a layer of carrier material is impregnated with a first solution or suspension of reagents in a first solvent and dried. Thereafter, the same carrier material is impregnated with a second solution or suspension of the remaining reagents in a second solvent which prevents interaction with reagents impregnated by the first solvent and dried. In this way, the reagents in the respective solutions are prevented from substantial interaction during preparation of the test device and thus do not react prematurely. In a particularly preferred embodiment certain first reagents are impregnated into a layer of carrier material using an aqueous solution of these first reagents. For the remaining reagents, a suitable organic solvent is used such as toluene, acetone, chloroform, methylene chloride, n-propanol and ethylene dichloride to prepare the second impregnation solution. This second impregnation solution is administered to the carrier which is then set by allowing the organic solvent to evaporate.

An example of this preferred embodiment is a method for preparing a homogeneous specific binding assay device for determining a ligand in a liquid sample by incorporating a carrier with a composition which includes a $\beta$-galactosyl-umbelliferone-ligand or ligand analog conjugate, $\beta$-galactosidase, and anti-sera to the ligand which method comprises (a) impregnating a carrier with an aqueous solution of $\beta$-galactosidase and antisera to the ligand and drying the carrier; and (b) impregnating the carrier of (a) with an acetone solution of $\beta$-galactosyl-umbelliferone-ligand or ligand analog conjugate and drying the carrier.

Where the carrier comprises additional layers, e.g., paper or other fibrous material, such layers may be maintained in laminar relationship by adhesives which permit fluid passage between layers. In preparing integral analytical elements using film formers, the additional layer(s) can be preformed separately and laminated to form the overall element. The material of the film layer(s) can be a composition comprising a plasticizer and a polymer suitable to impart dimensional stability. Layers prepared in such a manner are typically coated from solution or dispersion onto a surface from which the dried layer can be physically stripped. However, a convenient method which can avoid problems of multiple stripping and lamination steps is to coat an initial layer on a stripping surface or a support, as desired, and thereafter to coat successive layers directly on those coated previously. Such coating can be accomplished by hand, using a blade coating device, or by machine, using techniques such as dip or bead coating. If machine coating techniques are used, it is often possible to coat adjacent layers simultaneously using hopper coating techniques well known in the preparation of light sensitive photographic films and papers.

Blush polymer layers can be used as the film layer material. The film is formed on a substrate by dissolving a polymer in a mixture of two liquids, one of which is of a lower boiling point and is a good solvent for the polymer and the other of which is of a higher boiling point and is a nonsolvent or at least a poor solvent for the polymer. Such a polymer solution is then coated on the substrate, and dried under controlled conditions. The lower boiling solvent evaporates more readily and the coating becomes enriched in the liquid which is a poor solvent or nonsolvent. As evaporation proceeds, under proper conditions, the polymer forms as a porous layer. Many different polymers can be used, singly or in combination, for preparing porous blush polymer layers. Typical examples include polycarbonates, polyamides, polyurethanes and cellulose esters such as cellulose acetate. For layers such as those containing a label conjugate or other reagent, a coating solution or dispersion including the matrix and incorporated active materials can be prepared, coated as discussed herein and dried to form a dimensionally stable layer.

The thickness of any layer and its degree of permeability are widely variable and depend on actual usage. Dry thickness of from about 5 microns to 100 microns have been convenient, although more widely varying thickness may be preferable in certain circumstances. For example, if comparatively large amounts of interactive material, e.g., polymeric materials like enzymes, are required, it may be desirable to prepare slightly thicker layers.

It can also be desirable to include within a carrier one or more reflective layers, optionally absorptive to detecting radiation, such as to facilitate signal detection by reflection radiometry, e.g., reflection photometry or a similar technique. Such reflector can be provided by one of the above-described layers or it can be provided by an additional layer that may not have an additional function within the element. Reflective pigments, such as titanium dioxide and barium sulfate, can be used to advantage in a reflecting layer. Blush polymers can also constitute a suitable reflecting material. In one preferred aspect, blush polymer layers can also incorporate a pigment to enhance reflectivity or other functions. The amount of pigment that can be included in a layer together with a blush polymer is highly variable, and amounts of from about 1 to about 10 parts by weight of pigment per part by weight of blush polymer are preferred, with from about 3 to about 6 parts pigment per part of blush polymer being most preferred.

It can be advantageous to incorporate one or more surfactant materials, such as anionic and non-ionic surfactant materials, in the layers of the carrier. They can, for example, enhance coatability of layers formulations and enhance the extent and range of wetting in layers that are not easily wetted by liquid samples in the absence of an aid such as a surfactant.

As mentioned previously herein, the integral analytical elements can be self-supporting or coated on a support. The support can be opaque or transparent to light or other energy. A support of choice for any particular carrier will be compatible with the intended mode of signal detection. Preferred supports include transparent support materials capable of transmitting electromagnetic radiation of a wavelength within the region between about 200 nm and about 900 nm. The support need not, of course, transmit over the entire 200–900 nm region, although for fluorometric detection of analytical results through the support it is desirable for the support to transmit over a wider band or, alternatively, to transmit at the absorption and emission spectra of the fluorescent materials used for detection. It may also be desirable to have a support that transmits one or more narrow wavelenth bands and is opaque to adjacent wavelength bands. This could be accomplished, for example, by impregnating or coating the support with one or more colorants having suitable absorption characteristics.

5. DETECTABLE RESPONSE

As previously noted, many of the recently devised homogeneous specific binding assay systems provide, or can be readily adapted to provide, a detectable response such as a color change, chemiluminescence, or fluorescence related to the presence or amount of the ligand under assay in the liquid sample.

The term "detectable species", and similar terms as used herein, refer to atoms, chemical groups (i.e., a portion of a molecule) or chemical compounds that are themselves directly or indirectly detectable and the term "detectable response", and similar terms as used herein, refer to the detectable manifestation of the presence of such species. Examples are electromagnetic radiation signals such as fluorescence, phosphorescence, chemiluminescence, a change in light absorption, or reflectance in the visible spectrum thereby producing a visible color change, a change in light absorption or reflectance outside the visible range, such as in the ultraviolet or infrared range. As will be apparent to one skilled in the art of specific binding assays, the phrase "detectable response", as used herein, is intended in its broadest sense. In addition to electromagnetic radiations signals the term "detectable response" is also meant to include any observable change in a system parameter, such as a change in or appearance of a reactant, observable precipitation of any component in the test sample or a change in any other parameter, whether it be in the assay system or the test sample. Such other detectable responses include electrochemical responses and calorimetric responses. Moreover, the detectable response is one which can be observed through the senses directly or by use of ancillary detection means, such as a spectrophotometer, ultraviolet light-sensing equipment, fluorometer, spectrofluorometer, pH meter or other sensing means.

After the analytical result is obtained as a detectable change, it is measured, usually by passing the test element through a zone in which suitable apparatus for reflection, transmission or fluorescence photometry is provided. Such apparatus serves to direct a beam of energy, such as light, at the element. The light is then reflected from the element back to a detecting means or passes through the element to a detector in the case of transmission detection. In a preferred mode, the analytical result is detected in a region of the element totally within the region in which such result is produced. Use of reflection spectrophotometry can be advantageous in some situations as it effectively avoids optical interference from any residues, such as blood cells or urine sediment, which have been left on or in the layers of the element or from atypical urine colors. Conventional techniques of fluorescence spectrophotometry can also be employed if desired. Furthermore, transmission techniques can be used to detect and quantify the indicating reaction products by reacting a flow of radiant energy, for example, ultraviolet, visible or infrared radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the element can be used. Various calibration techniques can be used to provide a control for the analysis. As one example, a sample of a standard solution of the ligand under assay can be applied adjacent to the area where the drop of sample is placed in order to permit the use of differential measurements in the analysis.

EXAMPLES

The following examples describe experiments which were performed in developing the present invention. While they illustrate preferred embodiments, they are in no way to be interpreted as limiting the scope of the invention.

EXAMPLE I

Substrate-Labeled Fluorescent Immunoassay Element for Gentamicin

Gentamicin is a water-soluble, broad spectrum aminoglycoside antibiotic derived from *Micromonospora purpurea*, an actinomycete. Peak serum concentration, in micrograms/milliliter ($\mu$g/ml) is usually up to four times the single intramuscular dose, which is usually 1-3 milligram(s)/kilogram of body weight (mg/kg), administered three times daily. It is potentially nephrotoxic.

Conjugate Preparation

Figure 2:
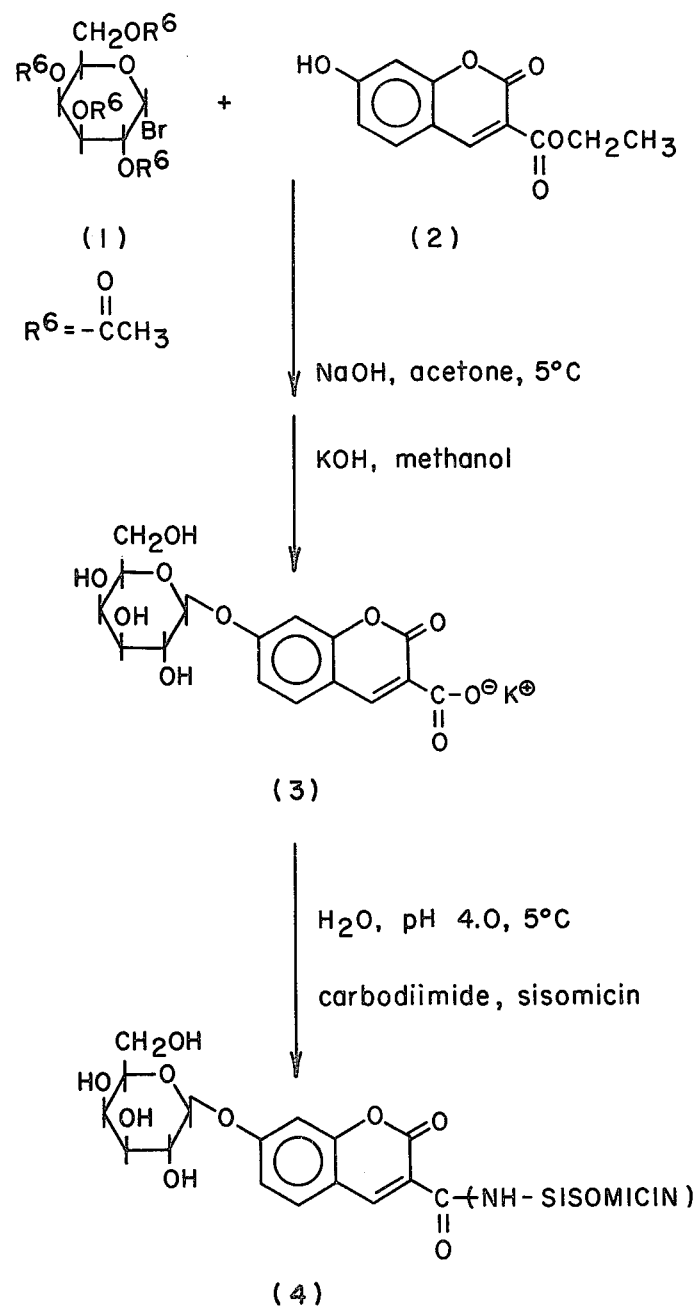

The reaction sequence for the preparation of the glycone-dye-drug conjugate is given in FIG. 2 in the drawings. 3-carboethoxy-7-hydroxycoumarin (2) was prepared by a Knoevenagel condensation of 2,4-dihydroxybenzaldehyde (Aldrich Chemical Co., Milwaukee, Wis., U.S.A.) with diethylmalonate in acetic acid, benzene, and piperidine as described in *J. Am. Chem. Soc.* 63:3452 (1971). The potassium salt of 7-$\beta$-galactosylcoumarin-3-carboxylic acid (3) was prepared by the reaction of 3-carboethoxy-7-hydroxycounarin (2) and 2,3,4,6-tetraacetyl-$\alpha$-D-galactosyl bromide (I, Sigma Chemical Co., St. Louis, Mo., U.S.A.) as described by Leaback for the preparation of methyl-umbelliferyl-$\beta$-D-galactoside in *Clin. Chim. Acta* 12:647 (1965). The potassium salt of this compound was purified by chromatography on silica gel-60 (E. Merck, St. Louis, Mo., U.S.A.) with a gradient of n-butanol/methanol/water (4/2/1 volume) and methanol/water (1/6). After recrystallization from acetone-water, the correct melting point of the product was 258°–263° C. (decomp.).

Analysis: Calculated for $C_{16}H_{15}O_{10}K$: C, 47,28: H, 3.73; K, 9.62. Found: C, 47.30; H, 3.74; K, 9.34. $[\alpha]_D = -77.4°$ (c 1.0, $H_2O$), NMR Spectrum ($D_2O$): $\delta$ 8.2 (s, 1H), 7.6 (m, 1H), 7.0 (m, 2H), 5.0 (s, 1H), and 4.0 (m, 6H).

Infrared Spectrum (KBr): 1705 cm$^{-1}$ (carbonyl), 1620 cm$^{-1}$ (C=C).

$\beta$-galactosyl-umbelliferone-sisomicin (4) was prepared by mixing 50 milligrams (mg) (117 $\mu$mol) of the potassium salt of 7-$\beta$-galactosylcoumarin-3-carboxylic acid (3) with 171 mg of sisomicin sulfate (223 $\mu$mol of sisomicin free base, Schering Corp., Bloomfield, N.J., U.S.A.) in 2 ml of water. The pH was adjusted to 3.8 by dropwise addition of 1 molar hydrochloric acid. The solution was cooled in an ice bath and 30 mg (150 $\mu$mol) of 1-ethyl-3-(3-dimethylaminopropyl)-carbodiimide hydrochloride (Pierce Chemical Co., Rockford, Ill., U.S.A.) was added. After 2 hours the mixture was chromatographed at 25° C. on a 2.5×50 centimeter (cm) column of CM-Sephadex C-25 (Pharmacia Laboratories, Inc., Piscataway, N.J., U.S.A.) 5.8 ml fractions were collected, and their absorbance was conitored at 345 nanometers (nm). The column was washed with 200 ml of 50 mmol/liter ammonium formate to elute unreacted 7-$\beta$-galactosylcoumarin-3-carboxylic acid (3). A linear gradient formed with 400 ml of 50 mmol/liter and 400 ml of 1.8 mol/liter ammonium formate, was applied to the column. A peak of material absorbing at 345 nm eluted at approximately 1.4 mol/liter ammonium formate. After the gradient, the column was washed with 600 ml of 1.8 mol/liter ammonium formate. Three 345 nm absorbing peaks were eluted in this wash. Eluted unreacted sisomicin was well separated from the last 345 nm absorbing peak.

The carbodiimide-activated reaction leads to the formation of amide bonds between the carboxylic acid of $\beta$-[7-(3-carboxy-coumarinoxy)]-galactoside and the primary amino groups of sisomicin. The major peak of $\beta$-galactosyl-umbelliferone-sisomicin (the last 345 nm absorbing peak) was used in the present studies. Ammonium formate was removed by lyophilization. Because the absorptivity of isolated label conjugate is currently unknown, the relative concentration is presented in terms of $A_{345}$ units. One $A_{345}$ unit is the quantity of material contained in 1 ml of a solution that has an absorbance of 1.0 at 345 nm when measured with a 1 cm light path.

Antiserum Preparation

Antiserum to gentamicin was prepared as described in *Nature New Biol.* 239:214 (1972).

Element Preparation

Aqueous Solution

To 5.00 milliliters (ml) of antiserum was added 6.4 ml of 1 molar N,N-bis-(2-hydroxyethyl)-glycine (Bicine) buffer (Nutritional Biochemicals Corp.) containing 0.1 molar magnesium chloride, and 2.84 ml of a 73.9 units/ml $\beta$-galactosidase solution. The pH was adjusted to 8.3 by adding 1.1 ml of a 0.16 molar sodium hydroxide solution. A sheet of Whatman 31 ET paper (Whatman, Inc. Clifton, N.J.) was impregnated to saturation with the above solution and dried at 50° C. for 15 minutes.

Organic Solution

The paper was then impregnated a second time with a conjugate solution prepared by adding 0.5 ml of 32.5 micromolar ($\mu$m) $\beta$-galactosyl-umbelliferone sisomicin conjugate solution in 0.05 molar sodium formate (pH 3.5) to 20 ml of acetone.

The resulting immunoreagent paper was laminated onto silver Mylar and one side of double-faced adhesive tape. After cutting into 1 centimeter (cm) ribbons the material was laminated onto one surface of 8.3×12.7 cm polystyrene supports. The laminated supports were cut into 8.3 cm×1 cm configuration each having 1 cm×0.5 cm assay element.

Final reagent contents per gentamicin immunoassay element were as follows:

| Component | Content |
| --- | --- |
| Antiserum | 7.7 $\mu$l |
| Conjugate | $\beta$-gal-umb-sisomicin |
| (quantity) | 65 picomoles |

| Component | Content |
| --- | --- |
| Buffer (bicine) | 10.8 micromoles |
| Magnesium chloride | 1.0 micromole |
| β-galactosidase | 0.33 units |
| Sodium formate | 0.1 micromole |

Analytical Procedure 35 microliter (μl) aliquots of drug solution were pipetted onto the exposed surface of the analytical elements prepared as described above.

The fluorescence generated at room temperature at the end of 15 minutes was measured in a fluorometer equipped with a mechanical holder suitable for horizontally positioning the analytical element. The fluorometer had been adjusted to provide an excitation light source at 405 nm, which struck the surface at 90° and to detect light emitted at a wavelength of 450 nm. A front face measurement of fluorescence was made at a 90° angle from the pad.

The concentration ranges assayed were as follows:

| RANGE | GENTAMICIN |
| --- | --- |
| Therapeutic Range | 5–10 μg/ml |
| Dose Response Range Checked | 0–5.0 μg/ml |

The dose response range checked covers the therapeutic range since solutions containing up to 10 μg/ml were checked after 1:2 dilution in distilled water.

Results

Figure 3:
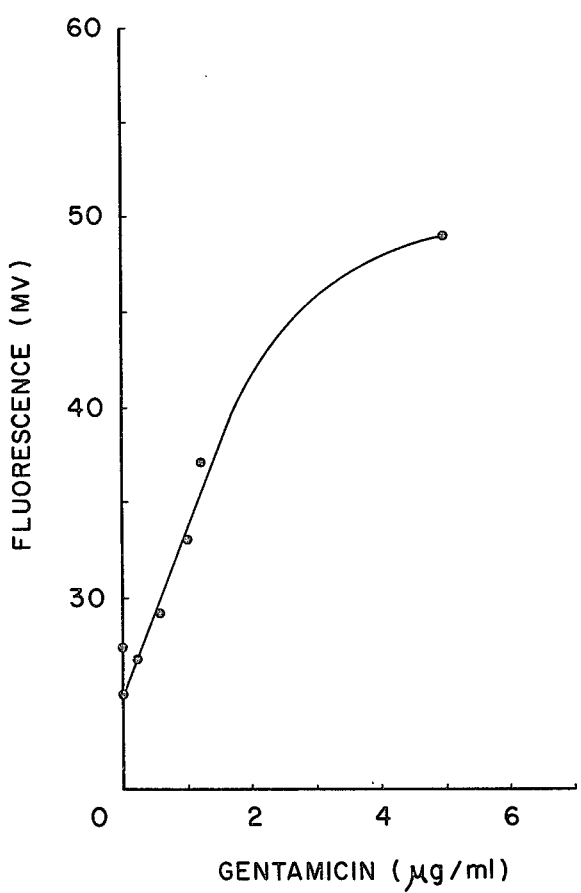

The data obtained by the above-described procedure are graphically illustrated by FIG. 3. The ordinate units are expressed in terms of millivolts (mv). A millivolt is one thousanth of a volt.

Conclusion

The resultant data show that integral analytical elements, prepared according to the invention provide quantitatively detectable signals which are responsive to the concentration ranges of the gentamicin present. Increasing concentrations of gentamicin results in a drug dependent increase in fluorescence of the respective analytical elements.

EXAMPLE II

Substrate-Labeled Fluorescent Immunoassay Element for Tobramycin

Tobramycin is another water-soluble, broad spectrum aminoglycoside antibiotic derived from *Streptomyces tenebrarius*, an actinomycete. Peak serum concentration (μg/ml) is usually up to four times the single intramuscular dose, which is usually 1–3 mg/kg administered three times daily. Like other aminoglycoside antibiotics, it is potentially nephrotoxic.

Conjugate Preparation

The reaction sequence and methodology for the preparation of the tobramycin conjugate were basically those of Example I.

With 55 mg (135 μmol) of the potassium salt of 7-β-galactosylcoumarin-3-carboxylic acid was mixed 150 mg (220 μmol) of tobramycin (Eli Lilly & Co, Indianapolis, Ind., U.S.A.) in 1.5 ml of distilled water. The pH was adjusted to 3.65 by the dropwise addition of 1 N hydrochloric acid and the resulting solution cooled in an ice bath. To initiate the coupling reaction, 30 mg (160 μmol) of 1-ethyl-3-(3-dimethylaminopropyl) carbodiimide hydrochloride were added. After overnight incubation of 4° C., two drops of 1 N sodium hydroxide were added to give a pH of 6.1.

The product was purified by chromatography on carboxymethyl Sephadex gel (Pharmacia Laboratories, Inc.) with ammonium formate as eluant. After an initial wash with 0.05 M ammonium formate to remove unreacted galactoside, 1.5 M ammonium formate was used to elute conjugated products. Five peaks of material absorbing at 345 nm were eluted, with the third peak being selected for use in this study.

Antiserum Preparation

Antiserum to tobramycin was prepared as described for gentamicin in *Nature New Biol.* 239:214 (1972).

Element Preparation

Preparation of the analytical element was as described in Example 1, with the exceptions that the conjugate and antiserum used were those prepared as described in this Example.

Final reagent contents per tobramycin immunoassay element were as follows:

| Component | Content |
| --- | --- |
| Antiserum | 7.7 μl |
| Conjugate | β-gal-umb-tobramycin |
| (quantity) | 59 picomoles |
| Buffer (bicine) | 10.8 micromoles |
| Magnesium chloride | 1.0 micromole |
| β-galactosidase | 0.33 units |
| Sodium formate | 0.5 micromoles |

Analytical Procedure

The procedure followed in performing the assays reported by this Example were identical with those described in Example 1.

The concentration ranges assayed were as follows:

| RANGE | TOBRAMYCIN |
| --- | --- |
| Therapeutic Range | 5–10 μg/ml |
| Dose Response Range Checked | 0–12 μg/ml |

The dose response range checked includes the therapeutic range after a 1:2 dilution.

Results

Figure 4:
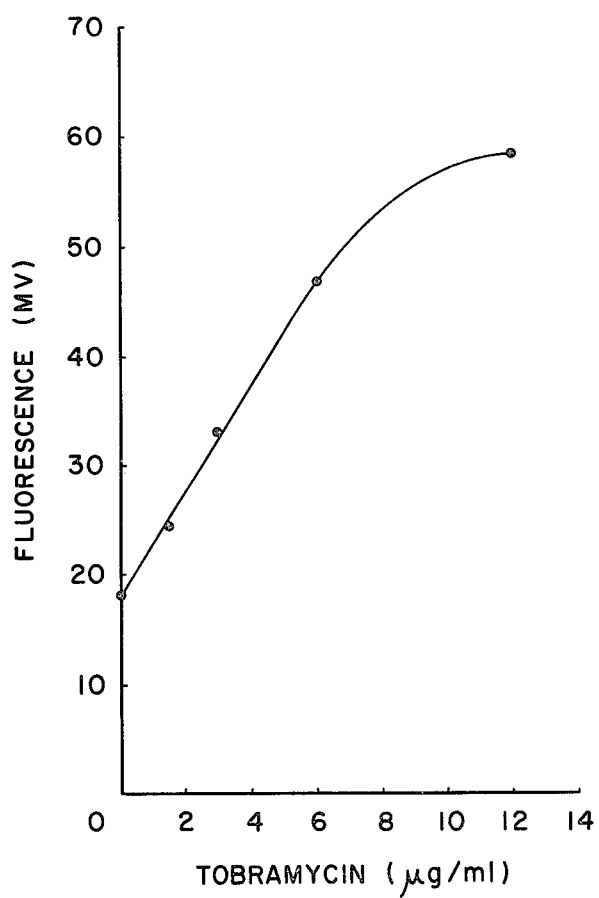

The data obtained by the above-described procedure are graphically illustrated by FIG. 4. The ordinate units are expressed in terms of electrical output.

Conclusion

The resultant data show that integral analytical elements, prepared according to the invention, provide quantitatively detectable signals which are responsive to the concentration ranges of the tobramycin present. Increasing concentrations of tobramycin results in a drug dependent increase in fluorescence of the respective analytical elements.

EXAMPLE III

Substrate-Labeled Fluorescent Immunoassay Element for Amikacin

Amikacin sulfate is a water-soluble, broad spectrum, semisynthetic aminoglycoside antibiotic derived from kanamycin, which is obtained from *Streptomyces kanamyceticus*. In normal adults, average peak serum concentrations of about 12, 16 and 21 µg/ml are obtained about 1 hour after intramuscular administration of 3.7 mg/kg, 5 mg/kg, and 7.5 mg/kg single doses, respectively. Normal dosage is 15 mg/kg daily, divided into 2–3 equal doses.

Conjugate Preparation

The reaction sequence and methodology for the preparation of the amikacin conjugate were basically those of FIG. 2.

290 mg (540 µmol) of amikacin (Bristol Laboratories, Syracuse, N.Y., U.S.A.) were mixed 110 mg (270 µmol) of the potassium salt of 7-β-galactosylcoumarin-3-carboxylic acid in 3 ml of distilled water. The pH was adjusted to 4.1 by addition of 1 N hydrochloric acid. After the solution had been cooled in an ice bath, 55 mg (292 µmol) of 1-ethyl-3(3-dimethylaminopropyl) carbodiimide hydrochloride were added to initiate the reaction. After overnight incubation at 4° C., the reaction mixture was chromatographed on carboxymethyl Sephadex gel. After washing the column with 0.05 M ammonium formate to remove unreacted galactoside, 1.5 M ammonium formate was used to elute the desired conjugate. Three peaks of material absorbing at 345 nm were obtained, with the last peak being used for this study.

Antiserum Preparation

Antiserum to amikacin was prepared as described for gentamicin in *Nature New Biol.* 239:214 (1972).

Element Preparation

Preparation of the analytical element was as described in Example 1, with the exceptions that the conjugate and antiserum used were those prepared as described in this Example and that the conjugate was dissolved in dimethylsulfoxide (DMSO).

Final reagent contents per amikacin immunoassay element were as follows:

| Component | Content |
|---|---|
| Antiserum | 7.7 µl |
| Conjugate (quantity) | β-gal-umb-amikacin 77.8 picomoles |
| Buffer (bicine) | 10.8 micromoles |
| Magnesium chloride | 1.0 micromole |
| β-galactosidase | 0.33 units |
| DMSO | 0.17 µl |

Analytical Procedure

The procedure followed in performing the assays reported by this Example were identical with those described in Example 1.

The concentration ranges assayed were as follows:

| RANGE | AMIKACIN |
|---|---|
| Therapeutic Range | 15–25 µg/ml |
| Dose Response Range Checked | 0–10 µg/ml |

The dose response range checked includes the therapeutic range after a 1:2 dilution.

Results

Figure 5:
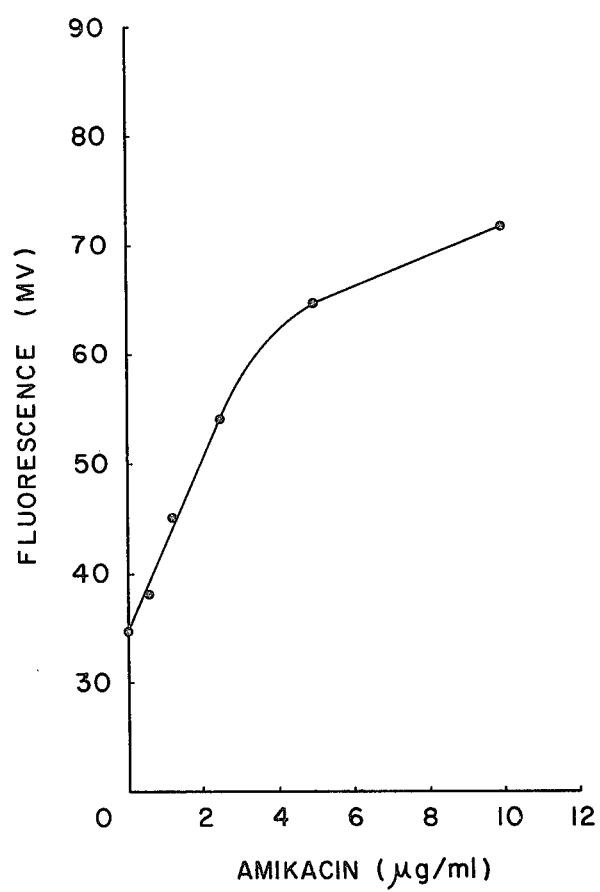

The data obtained by the above-described procedure are graphically illustrated by FIG. 5. The ordinate units are expressed in terms of electrical output.

Conclusion

The resultant data show that integral analytical elements, prepared according to the invention, provide quantitatively detectable signals which are responsive to the concentration ranges of the amikacin present. Increasing concentrations of amikacin result in a drug dependent increase in fluorescence of the respective analytical elements.

EXAMPLE IV

Substrate-Labeled Fluorescent Immunoassay Element for Theophylline

Theophylline [1,3-dimethylxanthine, cf. *The Merck Index*, 9th ed., p. 1196 (1976)] is a drug useful in the management of asthma. In most patients, the therapeutic range of serum concentration lies between 10 and 20 µg/ml whereas toxicity almost invariably appears at blood levels over 35 µg/ml.

Figure 6:
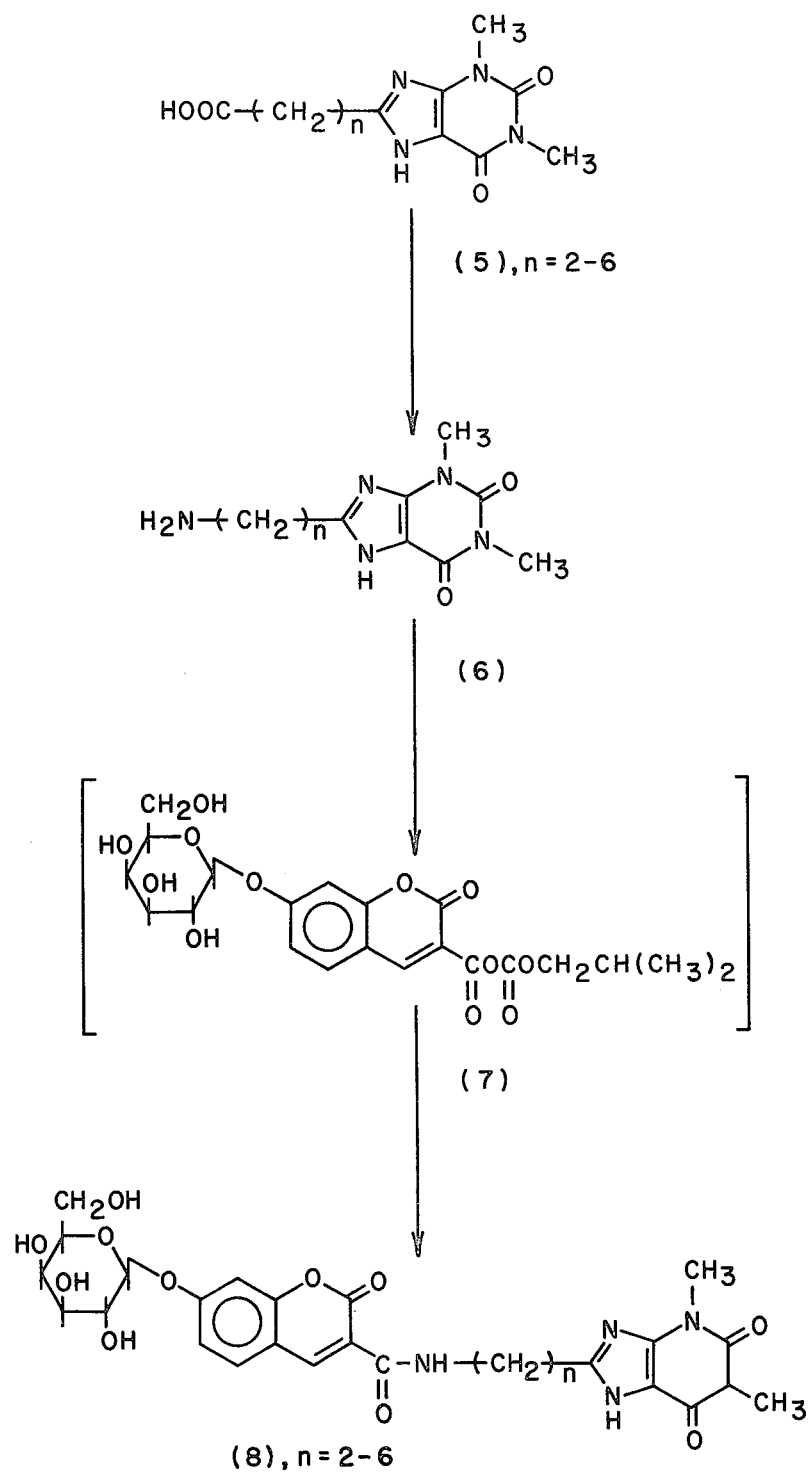

Conjugate Preparation

β-galactosyl-umbelliferone-labeled theophylline conjugates are prepared according to the reaction scheme shown in FIG. 6. This synthetic route is exemplified by the following method of preparing 8-[3-(7-β-galactosyl-coumarin-3-carboxamido)propyl]theophylline (8), n=3.

8-(3-Aminopropyl)theophylline (6)

A mixture of 2.66 g (0.01 mol) of 8-(3-carboxypropyl)theophylline (5) [Cook et al, *Res. Commun. Chem. Path. Pharmacol.* 13(3): 497–505 (1976)], 20 ml of chloroform, and 3 ml of concentrated sulfuric acid was stirred at 50° C. under an argon atmosphere. To this was added 1.3 g of solid sodium azide protionwise over a 90 minute period [cf. *Organic Reactions* 47:28 (1967)]. The reaction was cooled and the solvent removed under reduced pressure. The residue was combined with enough sodium bicarbonate solution to bring the pH to 7.5. Ten grams of celite (Fisher Scientific Co., Pittsburgh, Pa.) was added and the water evaporated. The impregnated celite was placed atop a column of 200 g of silica gel (E. Merck Co., Darmstadt, West Germany) made up in 9:1 (v:v) ethanol—1 molar aqueous triethylammonium bicarbonate. The column was eluted with this solvent and 15 ml fractions were collected. Fractions 171 to 225 were combined and evaporated to give 500 mg of a white powder. This substance was rechromatographed on a column of CM-Sephadex, ammonium form (Pharmacia Fine Chemicals, Piscataway, N.J., U.S.A.), eluting with 0.5 molar ammonium bicarbonate. The bed volume was 3 cm by 50 cm; and 10 ml fractions were collected. Fractions 65 to 110 were combined and evaporated to give 250 mg of a white solid. It was taken up in dilute hydrochloric acid, then reevaporated.

The residue was recrystallized from methanol to give 90 mg (3% yield) of the hydrochloric acid salt of (6) as pale tan needles that did not melt below 300° C.

Analysis: Calculated for $C_{10}H_{16}N_5ClO_2$: C, 43.88; H, 5.89; N, 25.59. Found: C, 43.77; H, 5.88; N, 25.46.

Infrared Spectrum (KCl): 1695 cm$^{-1}$ and 1655 cm$^{-1}$ (amide carbonyls).

8-[3-(7-$\beta$-galactosylcoumarin-3-carboxamido)propyl]-theophylline (8).

A reaction mixture was prepared containing 24 g of potassium hydroxide, 80 ml of water, 240 ml of methanol and 20 g (0.035 mmol) of ethyl 7-$\beta$-galactosylcoumarin-3-carboxylate [Burd et al, Clin. Chem. 23:1402 (1977)]. The reaction was stirred at 50° C. for 15 hours. When cool, the methanol was removed under reduced pressure. The concentrated aqueous solution was acidified to pH 2.0 with concentrated hydrochloric acid. The white precipitate was collected, washed with cold water, and recrystallized from hot water. The crystals were collected, washed with acetone, and dried at 80° C. for 1 hour. This gave 12 g of 7-$\beta$-galactosylcoumarin-3-carboxylic acid as white crystals, mp 250°–255° C.

A mixture of 1.45 g (0.004 mol) of 7-$\beta$-galactosylcoumarin-3-carboxylic acid, 404 mg (0.004 mol) of triethylamine, and 40 ml of dry dimethyl formamide (DMF) was cooled to −10° C. while stirring under argon. To this was added 546 mg (0.004 mol) of isobutyl chloroformate (Aldrich Chemical Co., Milwaukee, Wis.) to form the mixed anhydride (7). Ten minutes later, an additional 404 mg of triethylamine and 949 mg (0.004 mol) of 8-(3-aminopropyl)theophylline (6) was added to the flask. After stirring for 30 minutes at −10° C., the reaction was allowed to warm to room temperature. It was combined with 10 g of silica gel and the DMF removed under high vacuum. The impregnated silica gel was placed atop a column of 170 g of silica gel and the column eluted with anhydrous ethanol and collecting 15 ml fractions. Fractions 41 to 475 were combined and evaporated to give 545 mg of a yellow solid. It was dissolved in water, filtered, and concentrated to a 20 ml volume. A small amount of precipitate formed and was discarded. The filtrate was chromatographed on a 2.5 cm by 57 cm column of Sephadex LH-20 gel (Pharmacia Fine Chemicals, Piscataway, N.J.), eluting with water and collecting 15 ml fractions. Fractions 18 to 23 were combined, evaporated, and residue recrystallized from water to give 55 mg (2% yield) of the label conjugate (8) as a light yellow solid, mp 190°–192° C.

Analysis: Calculated for $C_{26}H_{29}N_5O_{11}$: C, 53.15; H, 4.98; N, 11.92. Found: C, 52.65; H, 5.01; N, 11.80.

The above-described synthesis of the $\beta$-galactosylcoumarin-theophylline conjugate (8), n=3, can be modified to yield label conjugates wherein n=2 through 6 by replacing the starting material 8-(3-carboxypropyl)-theophylline (5), n=3, with the appropriate 8-($\omega$-carboxyalkyl)theophylline as follows:

| n | Alkylene |
|---|----------|
| 2 | ethylene |
| 4 | butylene |
| 5 | pentylene |
| 6 | hexylene |

Antiserum Preparation

Antiserum was collected from rabbits immunized with a theophylline immunogen conjugate prepared as described by Cook et al, *Res. Comm. Chem. Path. Pharmacol.* 13:497–505 (1976).

Element Preparation

Preparation of the analytical element was as described in Example 1, with the exceptions that the conjugate and antiserum used were those prepared as described in this Example and that the conjugate was dissolved in dimethylsulfoxide (DMSO) rather than formate.

Final reagent contents per theophylline immunoassay element were as follows:

| Component | Content |
|-----------|---------|
| Antiserum | 7.7 µl |
| Conjugate (quantity) | $\beta$-gal-umb-theophylline 76 picomoles |
| Buffer (bicine) | 10.8 micromoles |
| Magnesium chloride | 1.0 micromole |
| $\beta$-galactosidase | 0.33 units |
| DMSO | 0.17 µl |

Analytical Procedure

The procedure followed in performing the assays reported by this Example were identical with those described in Example 1.

The concentration ranges assayed were as follows:

| RANGE | THEOPHYLLINE |
|-------|--------------|
| Therapeutic Range | 10–20 µg/ml |
| Dose Response Range Checked | 1–10 µg/ml |

The dose response range checked includes the therapeutic range after a 1:2 dilution.

Results

Figure 7:
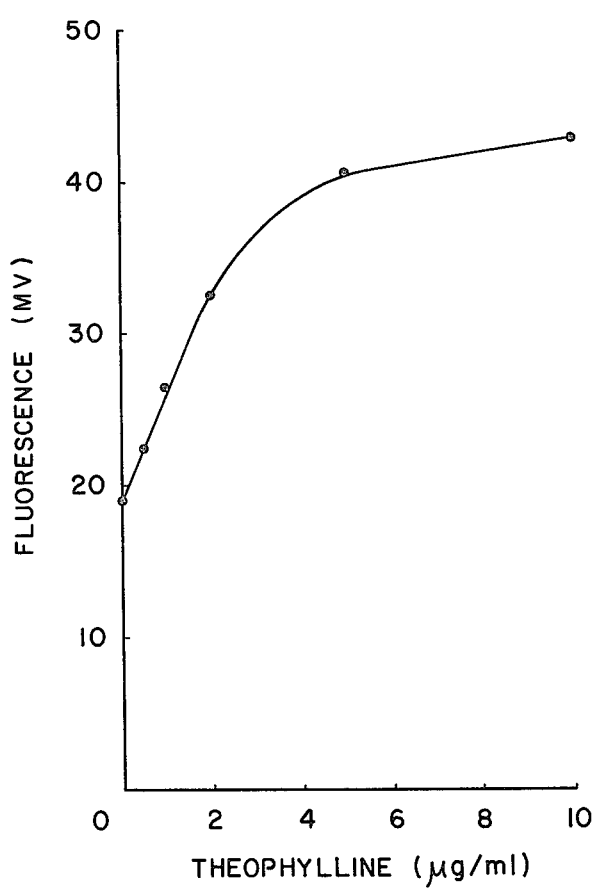

The data obtained by the above-described procedure are graphically illustrated by FIG. 7. The ordinate units are expressed in terms of electrical output.

Conclusion

The resultant data show that integral analytical elements, prepared according to the invention, provide quantitatively detectable signals which are responsive to the concentration ranges of the theophylline present. Increasing concentrations of theophylline results in a drug dependent increase in fluorescence of the respective analytical elements.

EXAMPLE V

Substrate-Labeled Fluorescent Immunoassay Element for Carbamazepine

Carbamazepine [5H-dibenz[b,f]azepine-5-carboximide, cf. *The Merck Index*, 9th ed., p. 226 (1976)] sold under various trademarks including Tegretol, is an anti-convulsant drug useful in the management of epilepsy. The therapeutic range of serum concentration in most patients lies between 8 and 12 μg/ml whereas toxic signs may appear at blood levels over 12 μg/ml.

Figure 8:
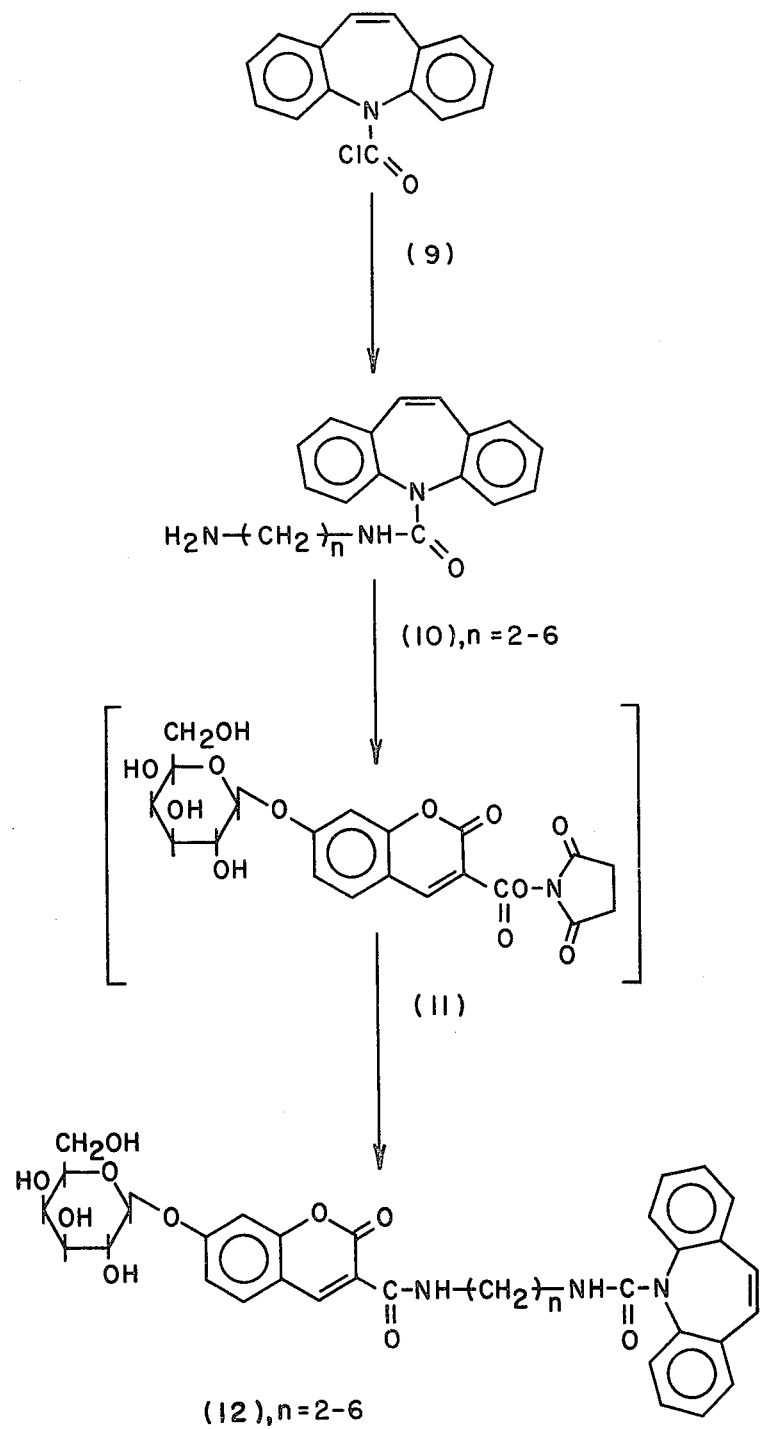

Conjugate Preparation

β-galactosyl-umbelliferone-labeled carbamazepine conjugates are prepared according to the reaction scheme shown FIG. 8 in the drawings. This synthetic route is exemplified by the following method of preparing N-[4-[7-β-galactosylcoumarin-3-carboxamido)]-butyl]aminocarbonyl-5H-dibenz[b,f]azepine (12), n=4.

N-(4-Aminobutyl)aminocarbonyl-5H-dibenz[b,f]azepine (10)

Phosgene gas was bubbled into a room temperature suspension of 14.1 g (0.073) of 5H-dibenz[b,f]azepine (Aldrich Chemical Co., Milwaukee, Wis.) in 180 ml of dry toluene until 15 g was absorbed. The warm mixture was stirred for 2 hours, heated at reflux for 2 hours, then stirred at room temperature overnight. The yellow solution, now containing N-chlorocarbonyl-5H-dibenz[b,f]azepine (9), was concentrated by boiling to about 100 ml volume. It was added dropwise over 1 hour to a solution at room temperature of 26 g (0.29 mol) of 1,4-diaminobutane in 250 ml of toluene. A white crystalline solid began to precipitate immediately. After the addition was complete, the resulting slurry was stirred at reflux for 3 hours. It was then cooled, filtered, and the precipitate washed with toluene. The filtrate was evaporated and excess butane diamine was removed by heating to 100° C. at 0.2 mm. The residual oil was taken up in dilute hydrochloric acid and some insoluble material filtered off. The solution was made basic to pH 9.5 with sodium carbonate and extracted with chloroform. Evaporation of this extract gave a glass that solidified when triturated with ether. This gave 15.8 g (70% yield) of the amine (10), as a solid, mp 114°–116° C.

Analysis: Calculated for $C_{19}H_{21}N_3O$; C, 74.24; H, 6.89; N, 13.67. Found: C, 73.92; H, 6.71; N, 13.64.

Infrared Spectrum (KCl); 1655 cm$^{-1}$ (amide carbonyl).

N-[4-(7-β-galactosylcoumarin-3-carboxamido)butyl]-aminocarbonyl-5H-dibenz[b,f]azepine (12).

A mixture of 24 g of potassium hydroxide, 80 ml of water, 240 ml of methanol, and 20 g (0.035 mol) of ethyl 7-β-galactosylcoumarin-3-carboxylate [Supra, Burd et al, *Clin. Chem.*] was prepared. The methanol was removed under reduced pressure. The concentrated aqueous solution was acidified to pH 2.6 with concentrated hydrochloric acid. The white precipitate was collected, washed with cold water, and recrystallized from hot water. The crystals were collected, washed with acetone, and dried at 80° C. for 1 hour. This gave 12 g (54% yield) of 7-β-galactosylcoumarin-3-carboxylic acid as white crystals, mp 250°–255° C.

A mixture of 1.02 g (5 mmol) of dicyclohexylcarbodiimide, 575 mg (5 mmol) of N-hydroxysuccinimide, and 50 ml of dry dimethylformamide (DMF) was stirred at room temperature under argon for 30 minutes. The clear, colorless solution was cooled to −5° and 1.835 g (5 mmol) of 7-β-galactosylcourmarin-3-carboxylic acid was added. The reaction was allowed to warm to room temperature and stirred for 2 hours. The mixture was then cooled in an ice bath and the precipitate of dicyclohexyl urea removed by filtration under argon. The filtrate, now containing the N-hydroxysuccinimide ester (11), was combined with 1.54 g (5 mmol) of N-(4-aminobutyl)aminocarbonyl-5H-dibenz[b,f]azepine, (10) dissolved in 5 ml of DMF. The reaction was stirred overnight at room temperature. The solvent was removed at 50° C./12 mm on the rotary evaporator and the residue triturated with dilute aqueous sodium bicarbonate solution. The insoluble material was chromatographed on 100 g of silica gel (E. Merck Co., Darmstadt, West Germany) eluting with a gradient of 2 L of ethyl acetate to 2 L of ethanol and 20 ml fractions were collected. Fractions 190 to 250 were combined, evaporated, and the residue recrystallized twice from ethanol. This gave 1.0 g (30% yield) of the label conjugate (12) as a white powder, mp 150°–160° C. (decomposed).

Analysis: Calculated for $C_{35}H_{35}N_3O_{10}$: C, 63.95: H, 5.35; N, 6.39. Found: C, 63.55; H, 5.77; N, 6.14.

Mass Spectrum (Filed desorption): m/e 658, [P+1].

Optical Rotation: $[\alpha]_D = -46.84°$ (c 1.0, MeOH).

The above-described synthesis of the β-galactosyl-coumarin-carbamazepine conjugate (12), n=4, can be modified to yield label conjugates wherein n=2 through 6 by replacing the starting material 1,4-diaminobutane with the appropriate α,ω-diaminoalkane as follows:

| n | α,ω-diaminoalkane |
|---|---|
| 2 | ethylenediamine |
| 3 | 1,3-diaminopropane |
| 5 | 1,5-diaminopentane |
| 6 | 1,6-diaminohexane |

Antiserum Preparation

Antiserum was obtained by immunization of rabbits with carbamazepine-bovine serum albumin immunogen conjugate.

Element Preparation

Preparation of the analytical element was as described in Example 1 with the exception that the conjugate and antiserum used were those prepared as described in this Example and that the conjugate was dissolved in DMSO.

Final reagent contents per carbamazepine immunoassay element were as follows:

| Component | Content |
|---|---|
| Antiserum | 7.7 μl |
| Conjugate | β-gal-umb-carbamazepine |
| (quantity) | 65 picomoles |
| Buffer (bicine) | 10.8 micromoles |
| Magnesium chloride | 1.0 micromole |
| β-galactosidase | 0.33 units |
| DMSO | 0.12 μl |

Analytical Procedure

The procedure followed in performing the assays reported by this Example were identical with those described in Example 1.

The concentration ranges assayed were as follows:

| RANGE | CARBAMAZEPINE |
|---|---|
| Therapeutic Range | 8–12 μg/ml |
| Dose Response | 0–1.25 μg/ml |

| RANGE | CARBAMAZEPINE |
|---|---|
| Range Checked | |

The dose response range checked includes the therapeutic range after a 1:10 dilution.

Results

Figure 9:
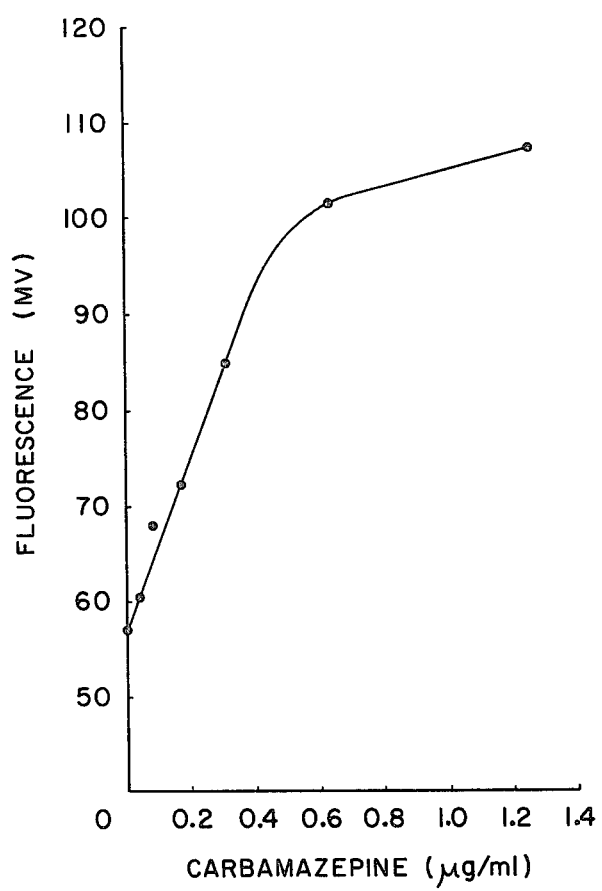

The data obtained by the above-described procedure are graphically illustrated by FIG. 9. The ordinate units are expressed in terms of electrical output.

Conclusion

The resultant data show that integral analytical elements, prepared according to the invention, provide quantitatively detectable signals which are responsive to the concentration ranges of the carbamazepine present. Increasing concentrations of carbamazepine result in a drug dependent increase in fluorescence of the respective analytical elements.

EXAMPLE VI

Substrate-Labeled Fluorescent Immunoassay Element For Primidone

Primidone [5-ethyl-5-phenylhexahydrophyrimidine-4,6-dione, cf. *The Merck Index*, 9th ed., p. 1003 (1976)], sold under various trademarks including Mysoline, is an anti-convulsant drug useful in the management of epilepsy. The therapeutic range of serum concentration in almost all patients lies between 5 and 10 $\mu$g/ml whereas toxicity almost invariably appears at blood levels over 15 $\mu$g/ml.

Conjugate Preparation

Figure 10:
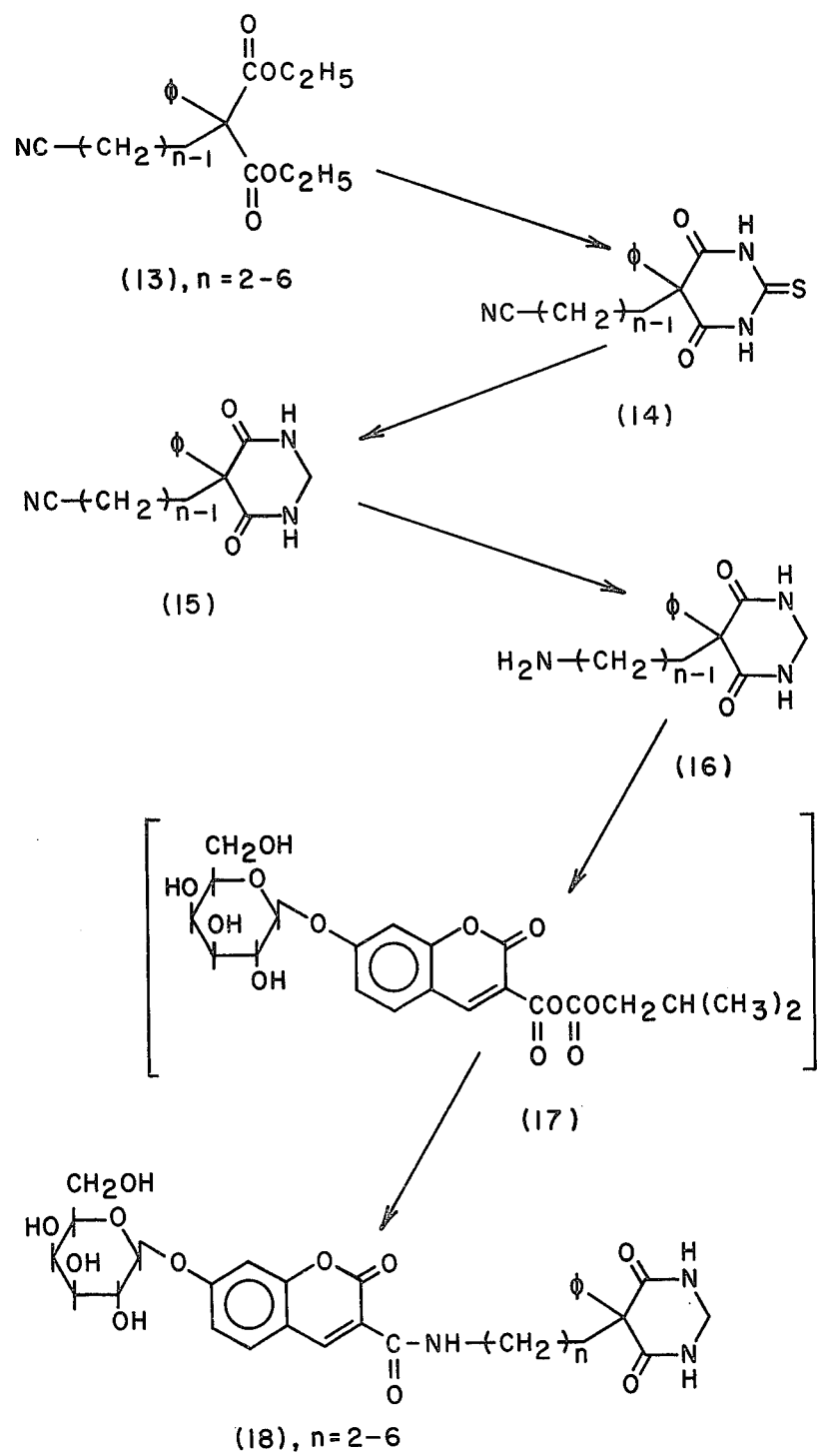

The $\beta$-galactosyl-umbelliferone labeled primidone conjugates are prepared according to the reaction scheme shown in FIG. 10 in the drawings. This synthetic route is exemplified by the following method of preparing 5-[4-(7-$\beta$-galactosylcoumarin-3-carboxamido)-butyl]-5-phenyl-2-desoxybarbituric acid (18), n=4.

Diethyl (3-Cyanopropyl)phenylmalonate (13)

A 50% mineral oil dispersion containing 16.8 g (0.7 mol) of sodium hydride was placed in a 3-liter, three-necked, round-bottom flask and washed free of oil with 500 ml of dry hexane. To this was added 1.2 liters of dry dimethylformamide (DMF) and 165.4 g (0.7 mol) of diethyl phenylmalonate (Aldrich Chemical Co., Milwaukee, Wis.). After hydrogen ceased to be evolved (3.5 hours), 104.2 g (0.7 mol) of 4-bromobutyronitrile (Aldrich Chemical Co.) was added, and the reaction heated at 65° C. overnight. The solvent was removed under reduced pressure, and the residue suspended in 1 liter of ethyl acetate. It was filtered, the filtrate reevaporated, and the residue evaporatively distilled at 170° C./0.1 mm to give 168 g (79% yield) of the diester (15) as a yellow liquid.

Analysis: Infrared Spectrum (CM 11$_3$): 2245 cm$^{-1}$ (CN); 1730 cm$^{-1}$ (ester carbonyl).

NMR Spectrum (CDCl$_3$): $\delta$ 1.3 (6H, t, J=8 Hz); $\delta$ 7.3 (5H, s).

5-(3-Cyanopropyl)-5-phenyl-2-thiobarbituric acid (14)

A solution of 11.5 g (0.5 g-atom) of sodium and 47.6 g (0.625 mol) of thiourea in 320 ml of absolute ethanol was stirred at reflux under an argon atmosphere. Over the next 30 minutes, 75.9 g (0.25 mol) of diethyl (3-cyanopropyl)phenylmalonate (13) was added dropwise. Heating was continued for 18 hours. When cool, the solvent was removed under reduced pressure, and the residue partitioned between 500 ml of water and 500 ml of ethyl acetate. The aqueous phase was separated, washed with ether, and acidified to pH 1 with concentrated hydrochloric acid. This aqueous mixture was allowed to evaporate to dryness to give a semicrystalline mass. It was digested with 350 ml of boiling chloroform, filtered, and cooled to give 20 g of light tan solid, mp 130°-145° C.

Recrystallization from ethanol gave 8 g (11% yield) of the cyano-thiobarbituric acid (14), as white crystals, mp 199° C.

Analysis: Calculated for C$_{14}$H$_{13}$N$_3$SO$_2$: C, 58.52; H, 4.56; N, 14.62. Found: C, 58.59; H, 4.39; N, 14.27.

Mass Spectrum (70 e.v.): m/e 287 [P$^+$]; m/e 240 [PH$^+$ minus CH$_2$CH$_2$CH$_2$CN].

5-(3-cynaopropyl)-5-phenyl-2-desoxybarbituric acid (15) and 5-(4-aminobutyl)-5-phenyl-2-desoxybarbituric acid (18).

A mixture of 8 g (0.029 mol) of 5-(3-cyanopropyl)-5-phenyl-2-thiobarbituric acid (16), 50 ml of an isopropanol slurry of freshly prepared W-5 raney nickel (R. L. Augustine, *Catalytic Hydrogenation*, Marcel Dekker, Inc., New York, 1965, page 27) and 300 ml of ethanol was stirred at reflux under a hydrogen atmosphere for 4 hours. It was filtered while hot and the filtrate cooled in an ice bath. The catalyst was washed with 200 ml of hot ethanol and then combined with the filtrate. When concentrated to a 50 ml volume, a yellow precipitate formed that amounted to 4.1 g when dry. This was chromatographed on 200 g of silica gel 60 (E. Merck Co., Darmstadt, West Germany). The column was eluted with 9:1 (v:v) toluene:methanol and 20 ml fractions were collected. Fractions 70 to 200 were combined, evaporated, and the residue twice recrystallized from ethanol to give 1.8 g (25% yield) of the cyano-desoxybarbituric acid (17) as fine white crystals, mp 253°-254° C.

Analysis: Calculated for C$_{14}$H$_{15}$N$_3$O$_2$: C, 65.35; H, 5.88; N, 16.33. Found: C, 65.09; H, 5.56; N, 15.71.

NMR Spectrum (d$_6$-DMSO): $\delta$ 4.0 (m, 2H); $\delta$ 7.4 (s, 5H).

The ethanol filtrate from the original crystallization was evaporated to give a glassy solid that was chromatographed on 250 g of silica gel using a solvent prepared by equilibrating equal volumes of chloroform, methanol, and concentrated ammonium hydroxide. The lower phase of this mixture was used to elute the column, and 15 ml fractions were collected. Fractions 66 to 100 were combined, evaporated, and the crystalline residue slurried in 2-propanol, filtered, and dried. This gave 180 mg (2% yield) of white crystals of the amino-desoxybarbituric acid (16), mp 242°-244° C.

Analysis: NMR Spectrum (d$_4$-CH$_3$OH):$\delta$ 3.0 (2H, t, J=8 Hz); $\delta$ 4.3 (2H, m); $\delta$ 7.3 (s, 5H)

Mass Spectrum (70 e.v.): m/e 261 [P$^+$]; 218 [P$^+$ minus CH$_2$=CHNH$_2$].

5-[4-(7-$\beta$-galactosylcoumarin-3-carboxamido)butyl]-5-phenyl-2-desoxybarbituric acid (18).

A mixture of 24 g of potassium hydroxide, 80 ml of water, 240 ml of methanol, and 20 g (0.035 mol) of ethyl 7-$\beta$-galactosylcoumarin-3-carboxylate [Burd et al, *Clin.*

*Chem.* 23:1402 (1977)] was stirred at 50° C. for 15 hours. When cool, the methanol was removed under reduced pressure. The concentrated aqueous solution was acidified to pH 2 with concentrated hydrochloric acid. The precipitate was collected, washed with cold water, and recrystallized from hot water. The crystals were collected, washed with acetone, and dried at 80° C. for 1 hour. This gave 12 g (54% yield) of 7-β-galactosyl-coumarin-3-carboxylic acid as white crystals, mp 250°-255° C.

A mixture of 210 mg (0.57 mmol) of 7-β-galactosyl-coumarin-3-carboxylic acid and 5.7 ml of 0.1 M solution of triethylamine in dry DMF was cooled to 10° C. while stirring under argon. To this was added 78 mg (0.57 mmol) of isobutyl chloroformate. After 15 minutes at −10° C., the reaction was allowed to warm to 0° C. for an additional 15 minutes. To this solution, now containing the mixed anhydride (17), was added 150 mg (0.57 mmol) of 5-(4-aminobutyl)-5-phenyl-2-desoxy-barbituric acid (16) and another 5.7 ml of 0.1 M triethylamine-DMF solution. The reaction was stirred at 0° C. for 15 minutes, then allowed to come to room temperature overnight.

Two gram of silica gel 60 was added to the reaction mixture and the solvent evaporated under high vacuum. The impregnated silica gel was placed atop a column of 50 g of silica gel made up in ethyl acetate. The column was eluted with a gradient of 1 liter of ethyl acetate to 1 liter of ethanol, and 10 ml fractions were collected. Fractions 120 to 160 were combined and evaporated to give a white solid. Recrystallization from methanol gave 180 mg (51% yield) of the label conjugate (18) as a white powder, mp 181°-183° C.

Analysis: Calculated for $C_{30}H_{33}N_3O_{11}$: C, 58.91; H, 5.44; N, 6.89. Found; C, 55.86; H, 5.28; N, 6.37.

Mass Spectrum (Field Desorption): m/e 612 [pH+].

Optical Rotation: $[\alpha]_D = -48.38°$ (c 1.0, $CH_3OH$).

The above described synthesis of the β-galactosyl-coumarin-primidone conjugate (20), n=4, can be modified to yield label conjugates wherein n=2 through 6 by replacing the starting material 4-bromobutyronitrile with the appropriate ω-bromoalkyl nitrile as follows:

| n | ω-bromoalkyl nitrile |
|---|---|
| 2 | 2-bromoacetonitrile |
| 3 | 3-bromopropionitrile |
| 5 | 5-bromovaleronitrile |
| 6 | 6-bromocapronitrile |

Antiserum Preparation

Antiserum was obtained by immunization of rabbits with a primidone-bovine serum albumin immunogen conjugate.

Element Preparation

Preparation of the analytical element was as described in Example 1 with the exception that the conjugate and antiserum used were those prepared as described in this Example and that the conjugate was dissolved in DMSO.

Final reagent contents per primidone immunoassay element were as follows:

| Component | Content |
|---|---|
| Antiserum | 7.7 µl |
| Conjugate (quantity) | β-gal-umb-primidone 67 picomoles |
| Buffer (bicine) | 10.8 micromoles |
| Magagnesium chloride | 1 micromole |
| β-galactosidase | 0.33 units |
| DMSO | .09 microliter |

Analytical Procedure

The procedure followed in performing the assays reported by this Example were identical with those described in Example 1.

The concentration ranges assayed were as follows:

| RANGE | PRIMIDONE |
|---|---|
| Therapeutic Range | 5–12 µg/ml |
| Dose Response Range Checked | 0–9 µg/ml |

The dose response range checked includes the therapeutic range after a 1:3 dilution.

Results

Figure 11:
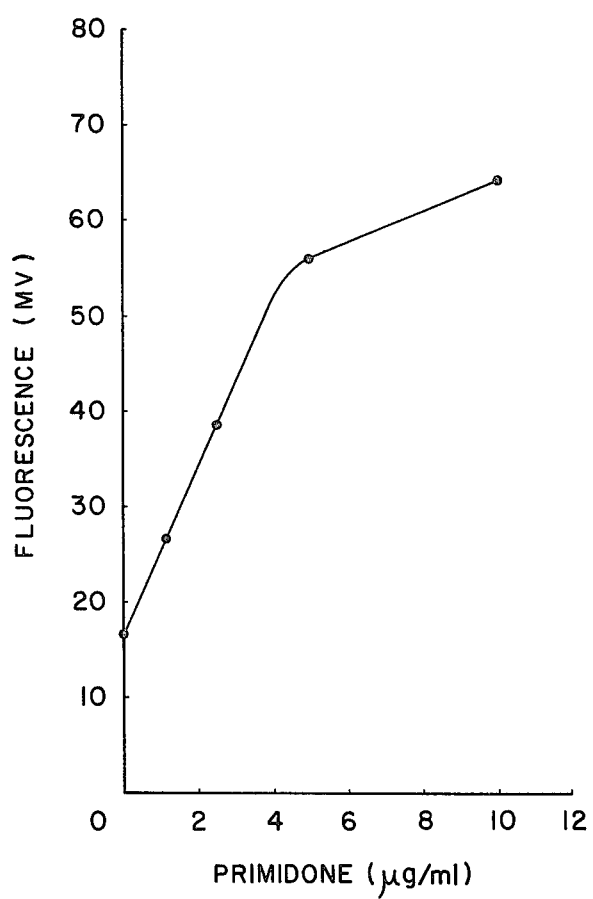

The data obtained by the above-described procedure are graphically illustrated by FIG. 11. The ordinate units are expressed in terms of electrical output.

Conclusion

The resultant data shown that integral analytical elements, prepared according to the invention, provide quantitatively detectable signals which are responsive to the concentration ranges of the primidone present. Increasing concentrations of primidone result in drug dependent increase in fluorescence of the respective analytical elements.

EXAMPLE VII

Fluorescence Quenching Immunoassay Element for Theophylline

In the experiment described by this example, a single layer element was prepared and tested for its ability to perform a direct quenching fluoroimmunoassay which quantitatively determined, as read by front face fluorometry, the presence of theophylline in a liquid sample.

Antiserum Preparation

Antiserum to theophylline was prepared by the method described in Example IV.

Conjugate Preparation

Umbelliferone-theophylline (conjugate) was prepared by hydrolysis of 0.16 mM galactosyl-umbelliferonetheophylline (GUT) by 0.1 U/ml β-galactosidase. GUT was prepared by the method described in Example IV.

Element Preparation

The solutions used in preparing the theophylline specific element contained the following components:

| Component | Content |
|---|---|
| Aqueous solution | |
| Antiserum | 50 µl |

-continued

| Component | Content |
| --- | --- |
| Double distilled water | 30 μl |
| Bicine, 0.5 M (pH 8.5) | 20 μl |
| Organic solution | |
| Toluene | 1.00 ml |
| Umbelliferone-theophylline (0.05 M, Bicine pH 8.5) | 4.00 μl |

A 1 cm×1 cm layer of Whatman 31 ET paper was laminated onto silver Mylar. The silver Mylar layer was then mounted, by double-faced adhesive tape, on a 8.3 cm×1 cm polystyrene support. Then, 20 μl of the above prepared aqueous solution was pipetted onto the layer of Whatman 31 ET paper. The paper was dried in a convection oven at 40° C. for 20 minutes. The organic solution (20 μl) was then pipetted onto the paper containing the dried residue of the aqueous solution and dried in a convection oven at 40° C. for 15 minutes.

Test Solution

Theophylline was added to aliquots of 0.05 M Bicine (pH 8.5) to give final theophylline concentrations of 0.125, 0.25, 0.50, 1.00, and 2.00 μg/ml, respectively.

Analytical Procedure

The analytical elements which had been prepared and fixed to supports as described above were inserted into a mechanical holder suitable for horizontally positioning the device in a fluorometer. Just prior to inserting the element and holder into the fluorometer, a 70 μl aliquot of one of the theophylline solutions, prepared as described above, was pipetted onto the exposed surface of the element.

The fluorometer had been adjusted to provide an excitation light source at 405 nm, which struck the surface of the element at a 90° angle, and to detect light emitted at a wavelength of 450 nm. A front face measurement of fluorescence was made at a 90° angle from the pad.

The fluorescence response of each was measured after 2 minutes.

Results

Figure 12:
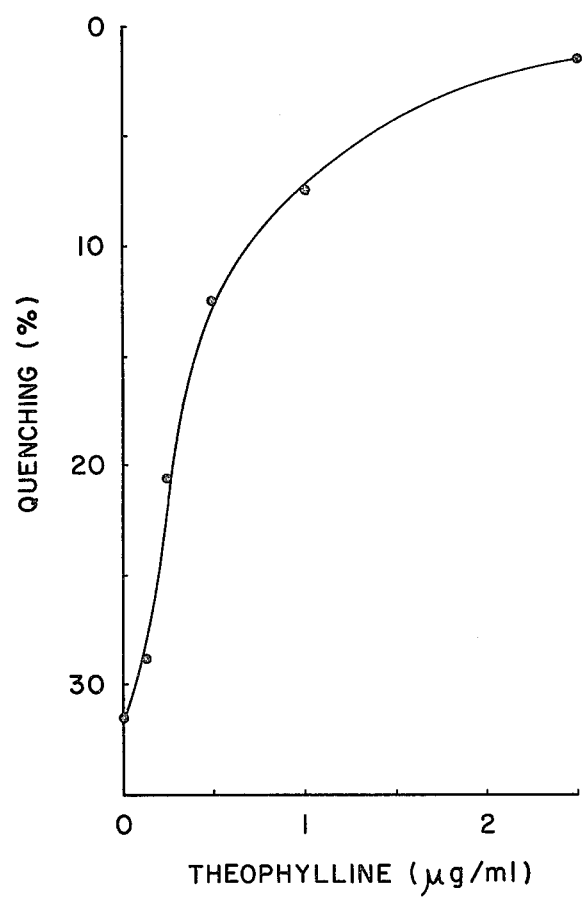

The data obtained in the above-described procedure are graphically illustrated by FIG. 12. The ordinate units are expressed as percent quenching.

Conclusion

The resultant data show that the analytical element provides a quantitatively detectable response to the theophylline concentration of each of the aliquots tested.

Under these conditions, fluorescence is quenched in the presence of antiserum and this quenching can be progressively overcome by increasing the concentration of theophylline.

EXAMPLE VIII

Prosthetic Group Label Colorimetric Immunoassay Element for Theophylline

In order to study various parameters of incorporating the prosthetic group label homogeneous immunoassay reagent system described in British Pat. No. 2,023,607 into a dry test device format, a theophylline specific system was experimentally devised. Reagents comprising the immunochemical components of the system included antibody to theophylline, a conjugate of theophylline and flavin adenine dinucleotide (FAD), and apoglucose oxidase.

The system was designed to respond to theophylline by exhibiting color due to the activation of apoglucose oxidase (formation of the holoenzyme) by the theophylline-FAD conjugate. Theophylline-FAD conjugate which does not become bound by antibody is directly proportional to theophylline concentration. It is detectable by its ability to combine with the apoglucose oxidase to produce active glucose oxidase enzyme. Thus, the response system included, in addition to apoenzyme, antibody and conjugate, a glucose oxidase detection system comprising glucose, 3,3',5,5'-tetramethylbenzidine (TMB), and horseradish peroxidase. Upon activation of the apoenzyme to glucose oxidase, a blue color formed due to the oxidation of glucose to hydrogen peroxide and subsequent conversion of TMB to its blue oxidized state in the presence of peroxidase.

Preparation of Apoenzyme

Apoenzyme was prepared from a sample of highly purified glucose oxidase obtained from Miles Laboratories, Inc. (Catalog No. 31-619). 10.5 milliliters (ml) of this enzyme solution (1000 units/ml) was mixed in a glass beaker with 4.5 ml of glycerol, and the mixture was cooled to a temperature of 0°-4° C. The pH of the mixture was lowered, using a 10% aqueous solution of sulfuric acid, until a pH of 1.4 was reached. This procedure was carried out with constant stirring with the beaker immersed in an ice bath, and the stirring was continued for 2 hours. After that time, the solution was poured over a 1.5 cm by 43 cm column of Sephadex G-50 (medium) cross-linked gel filtration media. The Sephadex had been equilibrated previous to the introduction of the enzyme solution with a 30% by volume aqueous glycerol solution having a pH of 1.4 Following the introduction of the enzyme solution onto the Sephadex column, more of the 30% glycerol solution was used to elute apoenzyme. The effluent was separated into fractions and observed using UV absorbance at 280 nanometers (nm). Those fractions having absorbance at this wavelength were combined with a buffer solution containing 50 milligrams (mg) of activated charcoal and 25 mg of dextran (Pharmacia Company No. T-70). The buffer comprised an aqueous solution which was 1 molar (M) tris-(hydroxymethyl)aminomethane to which glutamic acid was added until a pH of 7.0 was reached. The pH of the resultant effluent solution was then readjusted to 7 using a saturated solution of tris(hydroxymethyl)aminomethane. This final solution was allowed to stir in an ice bath for 1 hr. The apoenzyme solution was then centrifuged and the supernatant was filtered through 0.5 micrometer (μm) and 0.22 μm filters obtained from Millipore Corporation.

Conjugate Synthesis

The conjugate molecule whereby FAD is bound covalently to theophylline was prepared as follows. 1,3-Dimethyl-1,6,7,8-tetrahydropyrido[1,2e]-purine-2,4,9-[3H]-trione (0.9 mg/3.62 μmmol), prepared according to the method of Cook et al. was added to 0.2 ml dimethylsulfoxide containing 2.4 μmol and $N^6$-(aminohexyl) FAD. See Cook, C. E., Twine, M. E., Meyers, M., Amerson, E., Kepler, J. A. & Taylor, G. F. *Res. Commun. Chem. Path. Pharmacol.* 13, 497–505 (1976). After 4 hours a further 1.8 mg (7.3 μmol) of the trione was added. The solution was stirred overnight, the solvent evaporated under vacuum (0.1 mm Hg), and the residue chromatographed on a column (2.5×90 cm) of Sephadex LH-20 equilibrated with 0.3 M-triethylammonium bicarbonate (pH 7.8). The crude product, eluting between 216 and 246 ml of effluent, was collected, applied to a 20 cm×20 cm×100 μm silica gel plate and chromatographed using ethanol/1 M-triethylammonium bicarbonate, pH 7.8 (8:2 by volume). The band containing the desired product ($R_F$ 0.77) was scraped from the plate, extracted with 1 M-triethylammonium bicarbonate buffer, pH 7.8, filtered and concentrated. Final purification by chromatography on Sephadex LH-20 equilibrated with 0.3 M buffer gave 1.26 μmol of theophylline-FAD as determined by the absorbance at 450 nm, which represented a yield of 53%.

Antiserum Preparation

The antiserum to theophylline was collected from rabbits immunized with a theophylline immunogen conjugate as described by Cook, et al, *Res. Comm. Chem. Path. Pharmacol.* 13:497–505 (1976).

Element Preparation

Using this theophylline-FAD conjugate, reagent strips for the assay of theophylline were prepared. Pieces of Buckeye S-22 measuring 4 cm square were impregnated with a first dip solution comprising 5 mM TMB in acetone containing 0.1 gm per 100 ml of an emulsifier known as ON-870, marketed by General Aniline and Film Corporation. After dipping into the first dip solution, the impregnated papers were dried at 50° C. for 1 minute in a forced air oven.

Following drying, the papers were then impregnated with a second dip solution. The second dip was an aqueous solution which was adjusted to give a pH of 6.4, 0.1 M in glucose, 19 units/ml of horseradish peroxidase, glucose oxidase apoenzyme (1.0 nmoles FAD binding sites per ml), partially purified antibody to theophylline (0.14 ml antibody per ml dip solution), 0.5 mg/ml bovine serum albumin and 0.5 gm of polyvinyl alcohol per 100 ml. After brief immersion of the dried papers in the second dip solution, a second drying was effected at 50° C. for 12 minutes in a forced air oven.

The doubly impregnated papers were then further impregnated with a third solution containing FAD-theophylline conjugate at a concentration of 0.5 μM in acetone. These papers were then dried at 50° C. for 1 minute in the forced air oven.

Elements were prepared having 0.5 cm squares of the triply impregnated papers mounted on strips of polystyrene containing 0.5×8.3 cm utilizing double-faced adhesive known as Double-Stick (3M Company).

Test Solution

To test the performance of the test devices prepared above, solutions of theophylline in water were prepared having concentrations of theophylline in the range of 0.8 μM.

Analytical Procedure

The performance of the reagent device prepared and incubated as above-described was analyzed instrumentally using a device known as the "Rapid Scanner". This device is a scanning reflectance spectrophotometer interfaced with a PDP-12 computer obtained from the Digital Equipment Corporation. The instrument is used for the rapid measurement of reflectance spectra in the visual range. The computer allows for the storage of spectral data and computations.

The Rapid Scanner instrument was constructed by the Ames Company Division of Miles Laboratories, Inc., Elkhart, Ind. U.S.A., from whom complete information with respect to structural and performance characteristics are obtainable.

The elements were dipped in the test solutions and, after a period of 2 minutes, were analyzed using the Rapid Scanner. The reflectance data was obtained at 660 nm, which is the maximum absorption wavelength in the blue color range of oxidized TMB.

Results

Figure 13:
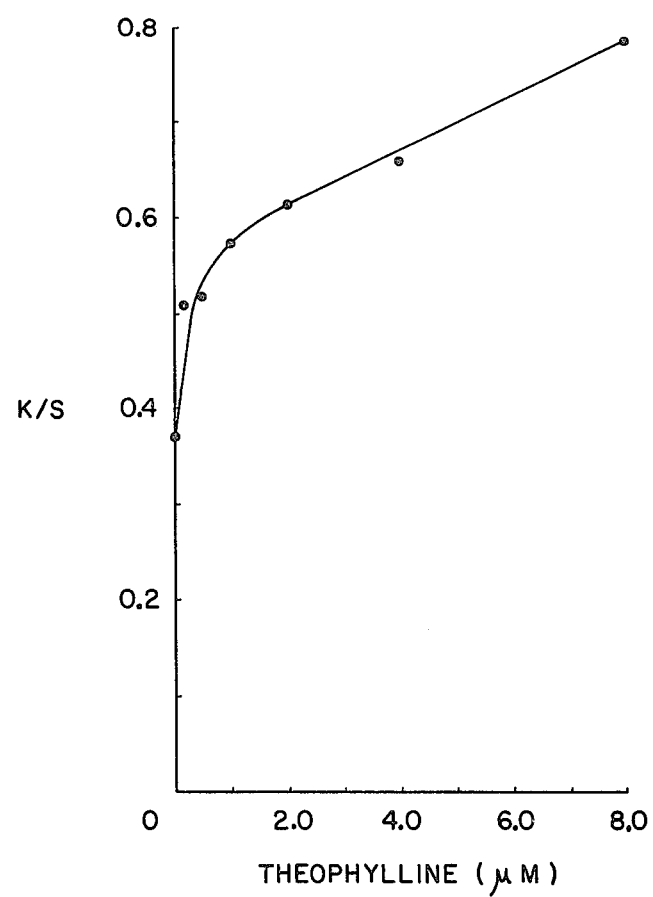

The dose-response curve is shown in FIG. 13 wherein K/S is plotted against theophylline concentration.

K/S is defined as follows:

$$\frac{K}{S} = \frac{(1-R)^2}{2R}$$

in which K is a constant, S is the scattering coefficient of the particular reflecting medium, and R is the fraction of reflectance from the test strip. This relationship is a simplified form of the well known Kubelka-Munk equation (Gustav Kortüm, "Reflectance Spectroscopy", pp. 106–111, Springer-Verlaz, New York (1969). K/S is a function of the colorant concentration. It increases with increasing ligand concentration, thereby indicating the efficacy of the device.

Conclusion

The plotted data shows that there is an observable color intensity change for varying amounts of theophylline in solution, and that the change is indicative of the particular theophylline concentration.

EXAMPLE IX

Prosthetic Group Label Colorimetric Immunoassay Element for Phenytoin

In the experiment described by this example, the same type of assay described in Example VIII was adapted to the quantitative determination of a different ligand, phenytoin.

Conjugate Preparation

To 14.7 mg (40.0 μmol) of 5-(2'-carboxybutyloxyphenyl-5-phenylhydantoin in 1.8 ml of molecular sieve-dried dimethylformamide (DMF), under argon, was added 0.10 ml (40.0 μmol) of a 400 μM solution of isobutyl chloroformate in DMF. The reaction was stirred one hour at room temperature. To the reaction mixture was added a solution of 10.0 μmol of $N^6$ (aminohexyl) FAD in 2.0 mol of molecular sieve-dried dimethylsulfoxide (DMSO), followed by 0.05 ml of a 400 μM solution of thioethylamine in DMF. The mixture was stirred 19 hours at room temperature, then was diluted to 450 ml with water and was applied to a 1.5 cm×30 cm column of Whatman DE-52 cellulose anion exchange resin (bicarbonate form) with the aid of a peristaltic pump. The column was then eluted with a gradient of 1.5 liters of water to 1.5 liters of 0.3 M triethylammonium bicarbonate aqueous solution. Fractions of approximately 16 ml were collected, with fractions 70–88 determined as containing the product on the basis of activity with apoglucose oxidase. These fractions were combined and the solution adjusted to pH 7. The yield was determined as 4.78 μmol (47.8% yield) on the basis of the absorbance of the solution at 450 nm using the millimolar extinction coefficient of FAD ($E_{450}=11.3$).

Antiserum Preparation

The antiserum was raised against o-caproyldiphenylhydantoin, similarly as in Example VIII.

Element Preparation

The test devices were prepared by consecutive immersion of a piece of paper into 3 solutions, each of which contained different components of an immunoassay system potentially responsive to the presence of phenytoin, with drying between each immersion.

Accordingly, a piece of paper measuring 4 cm square (S-22, Buckeye Cellulose Corp., Memphis, TN) was immersed in a 5 mM solution of TMB in acetone containing 0.1% (w/v) of an emulsifier known as OH-870 (General Aniline & Film Corp.). It was dried at 50° C. for 1 minute.

The paper was then immersed in a second, aqueous, solution which was 0.2 M in tris-glutamate buffer, pH 6.4, 0.1 M in glucose, horseradish peroxidase (19 units/ml), apoglucose oxidase (1.0 nmoles FAD binding sites/ml), 0.5 mg/ml bovine serum albumin, 0.5 g/100 ml polyvinyl alcohol (Type 20-30, Monsanto Co.,), and phenytoin antiserum (0.14 ml antiserum per ml).

After drying at 50° C. for 12 minutes in a forced air oven, the paper was impregnated by immersion in a third solution containing the FAD-phenytoin conjugate (0.5 μM) in n-propanol with 0.1 g/100 ml Gafquat 734, a polymer having pendant quaternary amine groups (General Aniline & Film Corp.).

Following drying at 50° C. for 3 to 4 minutes, the impregnated paper was used to make test strips having a 0.5 cm square of the reagent-laden paper mounted at one end of a strip of a polysyrene film measuring 0.5 by 8.3 cm. Mounting was achieved using a double-faced adhesive tape known as Double-Stick (3M Company).

Test Solution

The aqueous test solutions used contained the analyte at concentrations ranging from 0 to 8 μM.

Analytical Procedure

The elements were analyzed in the Rapid Scanner 2 minutes after inoculation as in Example VIII.

Results

Figure 14:
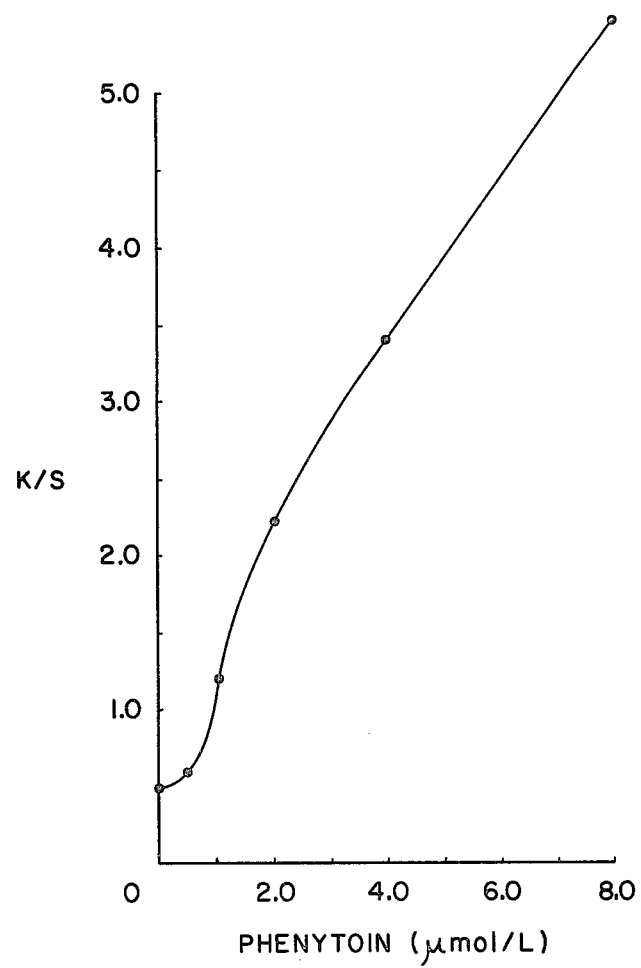

FIG. 14 shows the change in K/S with respect to phenytoin concentrations of 0, 0.5, 1, 2, 4 and 8 μM in water.

Conclusion

The data presented in FIG. 14 show that the test device responds well to the presence of phenytoin, enabling facile determination of different concentrations of the analyte, either instrumentally or visually.

What is claimed is:

1. A method for preparing a test device useful in performing a homogeneous specific binding assay to determine the presence of a ligand in, or the ligand binding capacity of, a liquid test sample, the method comprising the steps of
   incorporating a carrier with a first reagent mixture comprising water, a reagent capable of reacting with a label to produce a detectable response, and a specific binding partner to the ligand;
   drying the carrier incorporated with the first reagent mixture;
   incorporating the carrier with a second reagent mixture comprising a solvent selected from toluene, acetone, chloroform, methylene chloride, n-propanol and ethylene dichloride, and a label conjugate comprising the label coupled to a ligand moiety or a specific binding analogue thereof; and
   drying the carrier incorporated with the first and second mixtures.

2. The method of claim 1 wherein the reagent of the first reagent mixture comprises a component capable of cleaving the label from the label conjugate.

3. The method of claim 1 wherein the label is a fluor.

4. The method of claim 1 wherein the label is umbelliferone.

5. The method of claim 1 in which the reagent of the first reagent mixture comprises β-galactosidase and antibody to the ligand, the label is β-galactosyl-umbelliferone, and the solvent is acetone.

6. The method of claim 1 in which the ligand is an aminoglycoside antibiotic, the reagent of the first reagent mixture comprises β-galactosidase and antibody to the aminoglycoside antibiotic, the label is β-galactosyl-umbelliferone, and the solvent is acetone.

7. The method of claim 1 in which the ligand is gentamycin, the reagent of the first reagent mixture comprises β-galactosidase and antibody to gentamycin, the label is β-galactosyl-umbelliferone, and the solvent is acetone.

8. The method of claim 1 in which the ligand is tobramycin, the reagent of the first reagent mixture comprises β-galactosidase and antibody to tobramycin, the label is β-galactosyl-umbelliferone and the solvent is acetone.

9. The method of claim 1 wherein the label of the label conjugate is a substrate for an enzyme.

10. The method of claim 9 wherein the substrate is a β-galactoside moiety and the enzyme is β-galactosidase.

11. The method of claim 10 wherein the label is β-galactosyl-umbelliferone.

12. The method of claim 1 which further comprises, prior to incorporating the carrier with the first reagent mixture, the steps of
    incorporating the carrier with an indicator mixture comprising an indicator reactive with the reagent of the first reagent mixture to produce a detectable response, and a solvent selected from toluene acetone, chloroform, methylene chloride, n-propanol and ethylene dichloride; and
    drying the carrier incorporated with the indicator.

13. The method of claim 12 wherein the solvent is the same as that used to incorporate the carrier with the second reagent mixture.

14. The method of claim 12 wherein the indicator reagent comprises 3,3',5,5'-tetramethylbenzidine.

15. The method of claim 12 wherein the reagent of the first reagent mixture comprises glucose, glucose oxidase apoenzyme, peroxidase and antibody to the ligand, and the label comprises flavine adenine dinucleotide.

16. The method of claim 15 wherein the reagent of the first reagent mixture further comprises bovine serum albumin and polyvinyl alcohol.

17. An analytical element for determining a ligand in or the ligand binding capacity of a liquid sample, which element is prepared by the method of any of claims 1-8.

18. A method for determining the presence of a ligand in or the ligand binding capacity of a test sample, the method comprising contacting the test sample with a test device prepared by the method of any one of claims 1-8.

* * * * *